United States Patent [19]
Stillman et al.

[11] Patent Number: 6,074,819
[45] Date of Patent: Jun. 13, 2000

[54] DNA REPLICATION-REGULATING GENES

[75] Inventors: Bruce Stillman, Cold Spring Harbor, N.Y.; R. Sanders Williams, Dallas, Tex.

[73] Assignees: Cold Spring Harbor Laboratory, Cold Spring Harbor, N.Y.; Board of Regents, The University of Texas Systems, Austin, Tex.

[21] Appl. No.: 08/648,650

[22] Filed: May 15, 1996

Related U.S. Application Data

[63] Continuation-in-part of application No. 08/643,034, May 2, 1996.

[51] Int. Cl.$^7$ ............................ C12Q 1/68; A61K 31/00; A61K 38/00; C07H 21/04
[52] U.S. Cl. ............................... 435/6; 514/44; 536/23.1; 536/24.3; 536/24.33
[58] Field of Search ............................ 514/44; 536/23.1, 536/24.3, 24.33; 435/6, 91.2

[56] References Cited

FOREIGN PATENT DOCUMENTS

| | | |
|---|---|---|
| 07274971 | 10/1995 | Japan . |
| 93/10242 | 5/1993 | WIPO . |
| 93/23571 | 11/1993 | WIPO . |
| 94/23029 | 10/1994 | WIPO . |
| 95/16694 | 6/1995 | WIPO . |
| 95/21917 | 8/1995 | WIPO . |

OTHER PUBLICATIONS

Lee, C.C. and Caskey, C.T., "cDNA Cloning Using Degenerate Primers", In *PCR Protocols: A Guide To Methods and Applications*, Innis, M.A. et al., eds. (CA: Academic Press), pp. 46–53 (1990).
Donovan, S. and Diffley, J.F.X., "Replication origins in eukaroytes", *Current Opinion in Genetics & Development* 6(2):203–207 (1996).
Basco, R.D. et al., "Negative Regulation of $G_1$ and $G_2$ by S–Phase Cyclins of *Saccharomyces cerevisiae*", *Molecular and Cellular Biology* 15(9):5030–5042 (1995).
Williams, R.S. and Stillman, B., "Human and Xenopus Proteins Related To The Yeast CDC6/cdc18+ Regulators of DNA Replication", *Journal of Investigative Medicine* 44(3):198A (1996).
Williams, R.S. et al., "A human protein related to yeast Cdc6p", *Proc. Natl. Acad. Sci. USA* 94:142–147 (1997).
Coleman, T.R. et al., "The Xenopus Cdc6 Protein Is Essential for the Initiation of a Single Round of DNA Replication in Cell–Free Extracts", *Cell* 87:53–63 (1996).
Marx, J., "How DNA Replication Originates", *Science* 270:1585–1587 (1995).
Branch, A. D. A Good Antisense Molecule is Hard to Find. TIBS 23: 45–50, Feb. 1998.
Bell, S.P., et al., "The Multidomain Structure of ORC1p Reveals Similarity to Regulators of DNA Replication and Transcriptional Silencing," *Cell*, 83:563 (1995).

Bruschi, C.V., et al., "The Genomic Instability of Yeast cdc6–1/cdc6–1 Mutants Involves Chromosome Structure and Recombination," *Mol. Gen. Genet.*, 249:8–18 (1996).
Bueno, A. and Russell, P., "Dual Functions of CDC6: a Yeast Protein Required for DNA Replication Also Inhibits Nuclear Division," *EMBO*, 11:2167–2176 (1992).
Cocker, J.H., et al., "An Essential Role for the Cdc6 Protein in Forming the Pre–Replicative Complexes of Budding Yeast," *Nature*, 379:180 (1996).
Gavin, K.A., et al., "Conserved Initiator Proteins in Eukaryotes," *Science*, 270:1667–1671 (1995).
Hartwell, J., "Sequential Function of Gene Products Relative to DNA Synthesis in the Yeast Cell Cycle," *J. Mol. Biol.*, 15:803–817 (1976).
Hogan, E. and Koshland, D., "Addition of Extra Origins of Replication to a Miniochromosome Suppresses its Mitotic Loss in cdc6 and cdc14 Mutant of *Saccharomyces cerevisiae*," *PNAS*, 89:3098–3102 (1992).
Jallepalli, P. and Kelly, T., "RumI and Cdc18 Link Inhibition of Cyclin–Dependent Kinases to the Initiation of DNA Replication in S. pombe.," *Genes and Development*, 10:541–552 (1996).
Kelly, T.J., et al., "The Fission Yeast cdc18+ Gene Product Couples S. Phase to Start and Mitosis," *Cell*, 74:371–382 (1993).
Kelly, T.J., et al., "Coupling DNA Replication to the Cell Cycle," *Cold Spring Harbor Symp Quant. Biol.*, 58:637–644 (1993).
Leatherwood, J., et al., Interaction of Cdc2 and Cdc18 with a Fission yeast ORC2–Like Protein, *Nature*, 379:360 (1996).
Li, J.J. and Herskowitz, I, "Isolation of ORC6, a Component of the Yeast Origin Recognition Complex by a One–Hybrid System," *Science*, 262:1870–1874 (1993).
Liang, C., et al., "ORC and CdC6P Interact and Determine the Frequency of Initiation of DNA Replication in the Genome," *Cell* 81:667–676 (1995).
Lisziewicz, J. et al., "Cloning and Characterization of the *Saccharomyces Cerevisiae* CDC 6 Gene," *Nucleic Acids Research*, 16:11507–11520 (1988).
Muzi–Falconi, M., et al., "cdc18+ Regulates Initiation of DNA Replication in *Schizosaccharomyces pombe.*," *PNAS*, 93:1566–1570 (1996).
Nishitani, H. and Nurse, P., "p65$^{cdc18}$ Plans a Major Role Controlling the Initiation of DNA Replication in Fission Yeast," *Cell*, 83:397–405 (1995).

(List continued on next page.)

*Primary Examiner*—Nancy Degen
*Attorney, Agent, or Firm*—Hamilton, Brook, Smith & Reynolds, P.C.

[57] ABSTRACT

The invention pertains to novel genes which function in the regulation of DNA replication and/or entry of a cell into mitosis. The invention also pertains to novel proteins encoded by the genes described herein, antibodies which bind the encoded protein, and homologs of the novel genes which function in regulation of DNA replication and/or entry of a cell into mitosis and hybridize to the DNA sequence of the novel genes.

12 Claims, 10 Drawing Sheets

OTHER PUBLICATIONS

Palmer, R.E., et al., "Mitotic Transmission of Artificial Chromosomes in cdc Mutants of the Yeast, *Saccharomyces cerevisiae*," *Genetics*, 125:763–774 (1990).

Piatti, S., et al., "Cdc6 is an Unstable Protein Whose do novo Synthesis in $G_1$ is Important for the Onset of S Phase and for Preventing a 'Reductional' Anaphase in the Budding Yeast *Saccharomyces cerevisiae*," *EMBO*, 1141:3788–3799 (1995).

Zhou, C., et al., "Molecular Cloning of *Saccharomyces cerevisiae* CDC Gene: Isolation, Identification and Sequence Analysis," *J. Biol. Chem.*, 264:9022–9029 (1989).

Zwerschke, W., et al., "The *Saccharomyces cerevisiae* CDC6 Gene is Transcribed at Late Mitosis and Encodes a ATP/GTPase Controlling S Phase Initiation," *J. Biol. Chem.*, 269:23351–23356 (1994).

Antisense '97: A Roundtable on the State of the Industry Nature Biotechnology vol. 15 519–524, Jun. 1997.

Gura Antisense Has Growing Pains Science vol. 270 575–577, Oct. 1995.

Box 1

| | | | | | | | | |
|---|---|---|---|---|---|---|---|---|
| Kl | orc1 | G | T | P | T | V | G | K | T |
| Sc | orc1 | G | T | P | G | V | G | K | T |
| Hs | orc1 | G | V | P | G | T | G | K | T |
| Sp | orc1 | G | T | P | G | T | G | K | T |
| Sc | cdc6 | G | P | P | G | T | G | K | T |
| Sp | cdc18 | G | A | P | G | T | G | K | T |

Forward Primer:  5'- GGIGCCCCCGGIACCGGIAAAACC -3'
                     C A   A    A   G A
                     T T   T        T Box 3

| | | | | | | | | |
|---|---|---|---|---|---|---|---|---|
| Kl | orc1 | V | V | L | L | D | E | L | D |
| Sc | orc1 | V | V | L | L | D | E | L | D |
| Hs | orc1 | V | L | L | V | D | E | L | D |
| Sp | orc1 | V | V | L | M | D | E | L | D |
| Sc | cdc6 | V | V | V | L | D | E | M | D |
| Sp | cdc18 | I | I | V | L | D | E | M | D |

Forward Primer:  5'- ATCGTGCTCGACGAGATGG -3'
                     G T C  G  T A
                         T Box 4

| | | | | | | | | |
|---|---|---|---|---|---|---|---|---|
| Kl | ocr1 | L | D | L | P | E | R | H | L |
| Sc | orc1 | M | D | L | P | E | R | H | L |
| Hs | orc1 | M | D | L | P | E | R | I | M |
| Sp | orc1 | M | D | L | P | E | R | I | L |
| Sc | cdc6 | L | D | M | K | D | R | F | L |
| Sp | cdc18 | L | D | M | T | D | R | F | L |

Reverse Primer:  5' - AGAAAICGGTCIGTCATGTC -3'
                      G     TA T    A

```
         10         20         30         40         50         60         70
123 456 789 012 345 678 901 234 567 890 123 456 789 012 345 678 901 234 567 890 123 456 789 012 345 gag cgc ggc tgg agt ttg ctg ctg ccg ctg tgc tgc agt ttg ttc agg ggc ttg tgg cgg tga gtc cga gag gct gcg      75 tgt gag aga cgt gag aag gat cct gca ctg agg agg tgg aaa gaa gag gat tgc tcg agg agg cct ggg gtc tgt          150 gag aca gcg gag ctg ggt gaa ggc tgc ggg ttc cgg cga ggc ctg agc tgt gct gtc gtc ATG CCT CAA ACC CGA          225
                                                                                Met Pro Gln Thr Arg TCC CAG GCA CAG GCT ACA AGT TTT CCA AAG AGG CTG TCT CGG GCA TTG AAC AAA GCT AAA AAC TCC AGT                  300
Ser Gln Ala Gln Ala Thr Ser Phe Pro Lys Arg Leu Ser Arg Ala Leu Asn Lys Ala Lys Asn Ser Ser GAT GCC AAA CTA GAA CCA AAT GTC CAA ACC GTA ACC TGT TCT CCT CGT GTA AAA GCC CTG CCT CTC AGC CCC              375
Asp Ala Lys Leu Glu Pro Asn Val Gln Thr Val Thr Cys Ser Pro Arg Val Lys Ala Leu Pro Leu Ser Pro AGG AAA CGT CTG GGC GAT GAC AAC CTA TGC AAC ACT CCC CAT TTA CCT CCT TGT CCA AAG CAA GGC AAG                  450
Arg Lys Arg Leu Gly Asp Asp Asn Leu Cys Asn Thr Pro His Leu Pro Pro Cys Pro Lys Gln Gly Lys AAA GAG AAT GGT CCC CCT CAC TCA CAT ACA CTT AAG GGA CGA AGA TTG GTA TTT GAC AAT CAG CTG ACA ATT AAG          525
Lys Glu Asn Gly Pro Pro His Ser His Thr Leu Lys Gly Arg Arg Leu Val Phe Asp Asn Gln Leu Thr Ile Lys TCT CCT AGC AAA AGA GAA CTA GCC AAA GTT CAC CAA AAC ATA CTT TCT TCA GTT TCA GTT AGA AAA AGT CAA GAG ATC      600
Ser Pro Ser Lys Arg Glu Leu Ala Lys Val His Gln Asn Ile Leu Ser Ser Val Ser Val Arg Lys Ser Gln Glu Ile ACA ACA AAT TCT GAG CAG AAG CTG CCA CTG AAG AAA GAA TCT GCA TGT GTG AGA CTA TTC AAG CAA GAA GGC ACT          675
Thr Thr Asn Ser Glu Gln Lys Leu Pro Leu Lys Lys Glu Ser Ala Cys Val Arg Leu Phe Lys Gln Glu Gly Thr TGC TAC CAG CAA GCA AAG CTG CTG AAC ACA GCT GTC CCA GAT GTC AAA AAA GCT CGG CCT GCC AGG GAA AGG GAG ATG GAT  750
Cys Tyr Gln Gln Ala Lys Leu Leu Asn Thr Ala Val Pro Asp Val Lys Lys Ala Arg Pro Ala Arg Glu Arg Glu Met Asp GTC ATC AGG AAT TTC TTG AGG GAA CAC ATC ATT TGT GGA AGC CTT TAC CTT TCT GGT GCT CCT GGA                      825
Val Ile Arg Asn Phe Leu Arg Glu His Ile Ile Cys Gly Ser Leu Tyr Leu Ser Gly Ala Pro Gly ACT GGA AAA ACT GCC TGC TTA AGC ATT CGG CAA CTG AAG AAG CTC GAC CTG AAA CTG GAA CTG AAG CTG AAA ACT ATC ATG  900
Thr Gly Lys Thr Ala Cys Leu Ser Ile Arg Gln Leu Asp Leu Lys Lys Glu Leu Lys Lys Gly Phe Lys Thr Ile Met
```

FIG. 3B

```
                  10              20              30              40              50              60              70
    123 456 789 012 345 678 901 234 567 890 123 456 789 012 345 678 901 234 567 890 123 456 789 012 345
CTG AAT TGC ATG TCC TTG AGG ACT GCC CAG GCT GTA TTC CCA GCT ATT GCT CAG GAG ATT TGT CAG GAA GAG GTA     975
Leu Asn Cys Met Ser Leu Arg Thr Ala Gln Ala Val Phe Pro Ala Ile Ala Gln Glu Ile Cys Gln Glu Glu Val

TCC AGG CCA GCT GGG AAG GAC ATG ATG AGG ATG AAA TTG GAA AAA CAT GCA ACT ATG GAG GAG AAG GGC CCC ATG   1050
Ser Arg Pro Ala Gly Lys Asp Met Met Arg Met Lys Leu Glu Lys His Ala Thr Met Glu Glu Lys Gly Pro Met

TTG GTA TTG GAC GAG ATG GAT CAA CTG GAT GAC AGC AGT GAC CTA TTG TAC ACG TTG GTA TTT GAA TGG CCA TGG   1125
Leu Val Leu Asp Glu Met Asp Gln Leu Asp Asp Ser Ser Asp Leu Leu Tyr Thr Leu Val Phe Glu Trp Pro Trp

CTA AGC AAT TCT CAC TTG GTG CTG ATT GGT ATT GCT CTG GAT CTC ACA GAT CTA CCT AGG CTT   1200
Leu Ser Asn Ser His Leu Val Leu Ile Gly Ile Ala Leu Asp Leu Thr Asp Leu Pro Arg Leu

CAA GCT AGA GAA CTT AAT CAG GTA TGT AAG CCA CTG TTG AAC CCT TAT CCA AAT AGA CAG AAT CAA TTC TGT GCC AAA GTC   1275
Gln Ala Arg Glu Leu Asn Gln Val Cys Lys Pro Leu Leu Asn Pro Tyr Pro Asn Arg Gln Asn Gln Phe Cys Ala Lys Val

CAA GAT CGA CAG GTA TCT AAT CAG GAT AGA GCA CTG AAA GTT GAT GTT TGC AGG GTT GAA GCT GTA GAG TCA GAT GTC   1350
Gln Asp Arg Gln Val Ser Asn Gln Asp Arg Ala Leu Lys Val Asp Val Cys Arg Val Glu Ala Val Glu Ser Asp Val

TCT GCT GTT TCA GGA GAT GTT CGC AAA GCA CTG AAA GCT GTT TGC AGA GTT GAA GCT GTA GAG TCA GAT GTC   1425
Ser Ala Val Ser Gly Asp Val Arg Lys Ala Leu Asp Val Cys Arg Val Glu Ala Val Glu Ser Asp Val

AAA AGC CAG ACT ATT CTC AAA CCA CTG TCT GAA TGT TGT GAT GGT AAC AGG ATG ACC TTG AGC CAA GAG GGA CAA GAT   1500
Lys Ser Gln Thr Ile Leu Lys Pro Leu Ser Glu Cys Cys Asp Gly Asn Arg Met Thr Leu Ser Gln Glu Gly Gln Asp

CTT ATT CAC ATA TCC CAA CAG CAG CAG AAG CAG GTC ATC ATC TTG ATG CTC TTG ATG CTC TTG AAA ATC AAA GAG GTC   1575
Leu Ile His Ile Ser Gln Gln Gln Gln Lys Gln Val Ile Ile Leu Met Leu Leu Met Leu Leu Lys Ile Lys Glu Val

TCC TTC CCT CTT CAG CAG CAG AAG CAG GTC ATC ATC TTG ATG CTC TTG GTT TCT TTG ATG CTC TTG AAA ATC AGG CAG TTG AAA ATC AGG CAG GAG GTC   1650
Ser Phe Pro Leu Gln Gln Gln Lys Gln Val Ile Ile Leu Val Cys Ser Leu Met Leu Leu Arg Gln Leu Lys Glu Val

ACT CTG GGG AAG TTA TAT GAA GCC TAC AGT AAA GTC TGT CGC AAA CAG CAG GTG GCG GCT GTG GAC CAG TCA GAG   1725
Thr Leu Gly Lys Leu Tyr Glu Ala Tyr Ser Lys Val Cys Arg Lys Gln Gln Val Ala Ala Val Asp Gln Ser Glu
```

TGT TTG TCA CTT TCA GGG CTC TTG GAA GCC AGG GGC ATT TTA GGA TTA AAG AGA AAC AAG GAA ACC CGT TTG ACA    1800
Cys Leu Ser Leu Ser Gly Leu Leu Glu Ala Arg Gly Ile Leu Gly Leu Lys Arg Asn Lys Glu Thr Arg Leu Thr

AAG GTG TTT TTC AAG ATT GAA GAG AAA GAA ATA GAA CAT GCT CTG AAA GAT AAA GCT TTA ATT GGA AAT ATC TTA    1875
Lys Val Phe Phe Lys Ile Glu Glu Lys Glu Ile Glu His Ala Leu Lys Asp Lys Ala Leu Ile Gly Asn Ile Leu

GCT ACT GGA TTG CCT TAA att ctt ctc tta cac ccc acc cga aag tat tca gct ggc att tag aga gct aca gtc   1950
Ala Thr Gly Leu Pro *** ttc att tta gtg ctt tac aca ttc ggg cct gaa aac aaa tat gac ctt ttt tac ttg aag cca atg aat ttt aat   2025 cta tag att ctt taa tat tag cac aga ata ata tct ttg ggt ctt act att ttt acc cat aaa agt gac cag gta   2100 gac cct ttt taa tta cat tca ctt cta cca ctt gtg tat ctc tag cca atg tgc ttg caa gtg tac aga tct       2175 gtg tag agg aat gtg tgt ata ttt acc tct tcg ttt gct caa aca tga gtg ggt att ttt ttg ttt gtt ttt       2250 gtt gtt gtt gtt gag gcg cgt ctc acc ctg ttg ccc agg ctg gag tgc aat ggc gcg ttc tct gct cac tac       2325 agc acc cgc cca ggt tga agt gat tct ctt gcc tca gcc tcc cga gta gct ggg att aca ggt gcc cac cac       2400 cgc gcc cag cta att ttt taa ttt tta gta gag aca ggg ttt cac cat gtt ggc cag gct gtt ctt gaa ctc ctg   2475 acc ctc aag tga tct gcc cac ctt ggc ctc cct aag tgc tgg gat tat agg cgt gag cca cca tgc tca gcc att   2550 aag gta ttt tgt taa gaa ctt taa gtt tag ggt tag aag aat gat cca gaa aat gaa aaa tgc aag caa gtc cac   2625 atg gag att tgg agg aca ctg gtt aaa g
```

```
    123 456 789 012 345 678 901 234 567 890 123 456 789 012 345 678 901 234 567 890 123 456 789 012 345
                10              20              30              40              50              60              70
    ATG CCA AGC ACC AGG TCT CAA AGC TCC ATT CAG TTT CCC AAG AAA ACT CAG TCT ACG CTC GCC AAA      75
    Met Pro Ser Thr Arg Ser Gln Ser Ser Ile Gln Phe Pro Lys Lys Thr Gln Ser Thr Leu Ala Lys

GAG GTC TCA CGT GCA AAG AGC TCT GAG ATC TGC TCT GTC TCT CTC CCG CTC CCA CTT CCA AAA GAG     150
    Glu Val Ser Arg Ala Lys Ser Ser Glu Ile Cys Ser Val Ser Leu Pro Leu Pro Leu Pro Lys Glu

CTT CCC CTC AGT CCA CGC AAA CGG CTC GGT GAT GAC AAT CGT TGC AAC ATT CCT CCG ACA TTA AGC TGC TCC CCA     225
    Leu Pro Leu Ser Pro Arg Lys Arg Leu Gly Asp Asp Asn Arg Cys Asn Ile Pro Pro Thr Leu Ser Cys Ser Pro

CCC AAG CAG TCT CGC AAA GAG ACT CGC CAG CCA ACC CCT AAG GGG CGC CGT TTA CTT TTT GAT GAG AAC CAG     300
    Pro Lys Gln Ser Arg Lys Glu Thr Gly Gln Pro Thr Pro Lys Gly Arg Arg Leu Leu Phe Asp Glu Asn Gln

GCT GCA GCA GCG ACA CCA CTA TCC CCC CTC AAG CTA CAG GAT CCT TAT CTG CTG TCC CCT GTG AGA AAG GGG     375
    Ala Ala Ala Ala Thr Pro Leu Ser Pro Leu Lys Leu Gln Asp Pro Tyr Leu Leu Ser Pro Val Arg Lys Gly

CAA GAG ACC CCA CCC AGC TCT CGT AAG CAA AGG AAC AGT GTG GGG GTC CAG CTA TTT AAA CAG GAG GGC TCC TGC     450
    Gln Glu Thr Pro Pro Ser Ser Arg Lys Gln Arg Asn Ser Val Gly Val Gln Leu Phe Lys Gln Glu Gly Ser Cys

TAT CAG AAG GCT AAG CAC GCT TTG AAT ACG GCT ATA CCA GAG CGC CTG TTG GCT CGT GAG AGT GAG ACT GCA TTT     525
    Tyr Gln Lys Ala Lys His Ala Leu Asn Thr Ala Ile Pro Glu Arg Leu Leu Ala Arg Glu Ser Glu Thr Ala Phe

ATC AAG ACC TTC CTG ACA AGT CAT GTT TCT GCT GGG AAA GCC AAG GAT GAT GCT ATA TAC CTT GGT GCT CCT GGA ACT     600
    Ile Lys Thr Phe Leu Thr Ser His Val Ser Ala Gly Lys Ala Lys Asp Asp Ala Ile Tyr Leu Gly Ala Pro Gly Thr

GGG AAA ACT GCG TGC TTG AAT AAG CTG CTG CTG GAG GAG ACC AAG CTC AAG CAG TGC AAG ACC GTT TAC ATC     675
    Gly Lys Thr Ala Cys Leu Asn Lys Leu Leu Leu Glu Glu Thr Lys Leu Lys Gln Cys Lys Thr Val Tyr Ile

AAC TGC ATG TCA TTG CGC AGC GTG CAG GCA TCC CAG TTT CCG GCT ATA GCT GAA ATC TCT GGG GGC AAA TCT TCA     750
    Asn Cys Met Ser Leu Arg Ser Ser Gln Ala Val Phe Pro Ala Ile Ala Glu Ile Ser Gly Gly Lys Ser Ser

CTG GCC GCC AAA GAT ATT GTA AGG AGT TTG GAG AAG CTG ACT TCA AAG GGT CCA ATC ATC TTG CTG GTG TTG     825
    Leu Ala Ala Lys Asp Ile Val Arg Ser Leu Glu Lys Leu Thr Ser Lys Gly Pro Ile Ile Leu Leu Val Leu
```

GAT GAG ATG GAT CAG CTG GAC AGC AGA CAG GGA GAT GTC TTG TAC ACC GTG TTT GAG TGG CCT TGG CTT ACA AAT    900
Asp Glu Met Asp Gln Leu Asp Ser Arg Gln Gly Asp Val Leu Tyr Thr Val Phe Glu Trp Pro Trp Leu Thr Asn

TCT AGG ATG GTT TTA ATC GGC ATT GCT AAC GCA TTG GAT TTG ACA GAC CGT ATT TTG CCC AGG CTA CAA GCT CGA    975
Ser Arg Met Val Leu Ile Gly Ile Ala Asn Ala Leu Asp Leu Thr Asp Arg Ile Leu Pro Arg Leu Gln Ala Arg

CGT CCG TGC AGA CCA CAG TTG CTC AAC TTT TCT CCA TAT ACA AAG GAT CAG ATT GCT ACC ATT CTA CAG GAC AGA   1050
Arg Pro Cys Arg Pro Gln Leu Leu Asn Phe Ser Pro Tyr Thr Lys Asp Gln Ile Ala Thr Ile Leu Gln Asp Arg

CTA AAT ACG GTT TCA GGC GAT CAA GTT CTG GAT AAT GCT ATT CAG TTC TGT GCA AGG AAA ATC TCT GCT GTC   1125
Leu Asn Thr Val Ser Gly Asp Gln Val Leu Asp Asn Ala Ile Gln Phe Cys Ala Arg Lys Ile Ser Ala Val

TCT GGA GAT GCT CGA AAG CTA ACT GAA ATC TGC AGG AGA GCT GTT GAA ATT GTC GAA GCG GAT GTC AGG GGC CAG   1200
Ser Gly Asp Ala Arg Lys Leu Thr Glu Ile Cys Arg Arg Ala Val Glu Ile Val Glu Ala Asp Val Arg Gly Gln

ACT GTC CTT AAG CCT CTA ACT CTG GCG TCT CCT TGT CCA TTA AAC GAA GTC CCA CCT GTT CCA AAA AAG GTC   1275
Thr Val Leu Lys Pro Leu Thr Leu Ala Ser Pro Cys Lys Glu Val Pro Leu Asn Pro Val Pro Lys Val

AGC CTT CCA CAC ATC TCT CGT GTC CTG TCG GAT GTG TAT GGG GAC AAG ATG GCA AGC CGT GAG GGT TCA AGC GAG   1350
Ser Leu Pro His Ile Ser Arg Val Leu Ser Asp Val Tyr Gly Asp Lys Met Ala Ser Arg Glu Gly Ser Ser Glu

AGT TTT CCC TTA CAG CAG AAA                                                                          1371
Ser Phe Pro Leu Gln Gln Lys
```

DNA REPLICATION-REGULATING GENES

RELATED APPLICATIONS

This application is a continuation-in-part application of U.S. patent application Ser. No. 08/643,034, filed May 2, 1996 now U.S. Pat. No. 5,851,821 the entire teachings of which are incorporated herein by reference.

GOVERNMENT SUPPORT

Work described herein was supported by grant P01 CA 13106 from the National Cancer Institute. Work described herein was also supported, in whole or in part, by Grant Nos. RO1-AR40849, RO1-HL54794, P50-HL55988 and PO1-HL06296 from the National Institutes of Health. The U.S. Government has certain rights in the invention.

BACKGROUND OF THE INVENTION

Proliferative growth of normal cells requires an orderly progression through a series of distinct steps, a process known as the cell cycle (Alberts et al., *Cell Growth and Division,* Garland Publishing, Inc., New York). Progression through the cell cycle is modulated by nutrient availability, cell size, and growth factors through complex signaling pathways involving phosphorylation cascades and the strictly regulated expression and stability of specific proteins required at each phase of the cell cycle. In addition, the sequence of cell cycle events is rigorously controlled at specific checkpoints to ensure that each discrete stage in the cell cycle has been completed before the next is initiated. Human diseases associated with abnormal cell proliferation result when these rigorous controls on cell cycle progression are perturbed.

SUMMARY OF THE INVENTION

The invention relates to novel genes which function in cell cycle regulation. In a particular embodiment, the genes are derived from vertebrates, including mammalian cells, particularly those derived from Xenopus or human cells, and function in the regulation of DNA replication and/or entry of a cell into mitosis. In one embodiment, the gene is a human gene called Hscdc6 and in another embodiment the gene is a Xenopus gene called Xcdc6. In one embodiment, the genes have a DNA sequence comprising the DNA sequence of SEQ ID NO: 1 or SEQ ID NO: 3; the invention also pertains to the complementary DNA sequences of SEQ ID NOS: 1 and 3. The present invention also relates to genes which function in the regulation of DNA replication or the entry of a cell into mitosis and which have a nucleotide sequence which hybridizes under conditions of medium stringency to a DNA sequence of SEQ ID NO: 1 or SEQ ID NO: 3.

The invention also pertains to novel gene products, e.g., polypeptides or proteins, encoded by the vertebrate genes described herein. In a particular embodiment, the polypeptide or protein has the amino acid sequence of SEQ ID NO: 2 or SEQ ID NO: 4. In another embodiment, the gene product is a recombinant human or Xenopus polypeptide or protein which regulates DNA replication and/or the entry of a cell into mitosis. The invention also relates to vectors for expressing the described proteins or polypeptides and to host cells transformed with the vectors described. The invention further pertains to antibodies which bind the proteins and polypeptides described herein.

Furthermore, the invention encompasses pharmaceutical compositions comprising the genes and proteins or polypeptides described herein, as well as methods of treating disease utilizing the compositions described herein. For example, the invention relates to a method of treating a tumor in an individual. In the method, an antagonist of Hscdc6 is administered to the individual, causing at least one of two possible results: inhibition of Hscdc6 function and inhibition of tumor cell DNA replication, with concomitant inhibition of tumor growth, or mitotic division of tumor cells with failure of DNA replication and tumor cell death.

The invention also relates to a method of treating a tumor in an individual comprising administering an agonist of Hscdc6 to the individual in such a manner that it enters tumor cells in the individual; introduction of the Hscdc6 agonist in G2 or M phase of the cell cycle prevents entry of the cell into mitosis, and thus results in tumor cell death. The invention also pertains to a method of inhibiting undesired cell proliferation in an individual comprising administering an agonist or antagonist of Hscdc6 to the individual in such a manner that the agonist or antagonist enters the cells in which it is desirable to inhibit proliferation. An antagonist of Hscdc6 will prevent or reduce the activity of Hscdc6, and thereby prevent the replication of cellular DNA; cells with unreplicated DNA will enter mitosis and cell death will result. An agonist of Hscdc6 will prolong or increase the effects of Hscdc6, resulting in polyploidy and preventing mitosis; cells which are affected in this manner will undergo programmed cell death. The method of inhibiting cell proliferation can be used in the treatment of conditions associated with undesirable levels of cell proliferation.

The invention also encompasses a method of enhancing cell proliferation for therapy of a condition associated with loss of viable tissue in an individual comprising administering Hscdc6 or an agonist of Hscdc6 to an individual such that it enters cells in the individual. The activity of Hscdc6 or an Hscdc6 agonist causes initiation of DNA replication in the cell and entry of the cell into mitosis. The invention further relates to a method of diagnosing or aiding in the diagnosis of conditions associated with proliferative disorders in an individual; this method can also be used to predict the likelihood that an individual is at increased risk for a particular condition associated with abnormal cell proliferation. According to this method, by combining probes derived either from the isolated native sequence of the Hscdc6 gene or from the primers disclosed herein, with DNA from an individual to be assessed, under conditions suitable for hybridization, it can be determined whether the individual possesses the intact gene. Similarly, hybridization conditions can be selected such that the probes will hybridize only with altered DNA and not with unaltered DNA; that is, the probes can be designed to recognize only particular alterations in the nucleic acid sequence of the gene, including addition of one or more nucleotides, deletion of one or more nucleotides or change in one or more nucleotides (including substitution of a nucleotide for one which is normally present in the sequence).

BRIEF DESCRIPTION OF THE DRAWINGS

FIG. 1 illustrates the design of oligonucleotide primers for cloning of the genes described herein. Amino acid sequences from ORC1 proteins from *K. lactis* (Kl), *S. cerevisiae* (Sc), human (Hs) and *S. pombe* (Sp) were aligned in the region of three sequence blocks (Boxes 1, 3 and 4) which are conserved among these proteins, as well as cdc6p and cdc18+.

FIGS. 3A and 3B and 3C illustrate the complete cDNA (SEQ ID NO: 1) and predicted amino acid (SEQ ID NO: 2) sequences of Hscdc6. The putative initiation codon and the first in-frame stop codon are boxed.

FIGS. 4A and 4B illustrate a multiple sequence alignment of Hscdc6, Xcdc6 and related proteins from S. cerevisiae and S. pombe. Amino acid residues that are identical in both vertebrate proteins, or in one or both vertebrate proteins and one or both fungal proteins, are indicated by dark shading, and conservative substitutions are indicated by light shading. Conserved sequence boxes are enclosed. Areas previously known to be conserved among fungal cdc6p proteins and cdc18 and among fungal and human orc1p are designated Box 1 through Box 6. Other highly conserved regions newly identified are designated as CSH boxes.

FIGS. 6A and 6B illustrate the partial cDNA sequence (SEQ ID NO: 3) and predicted amino acid sequence (SEQ ID NO: 4) of Xcdc6.

DETAILED DESCRIPTION OF THE INVENTION

Figure 2:
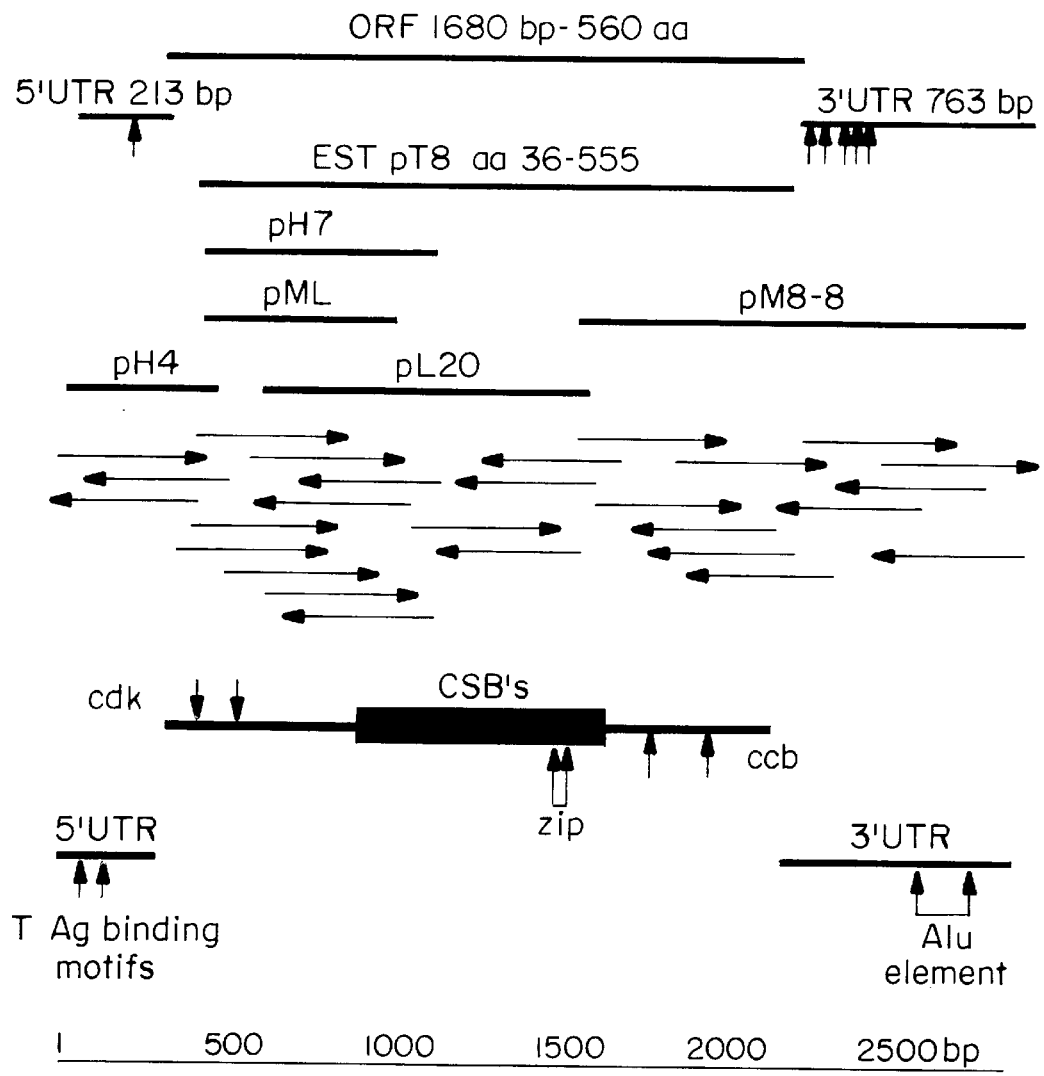
FIG. 2 illustrates the cloning results and sequencing strategy. In-frame stop codons are indicated with dark arrows pointing upwards. Horizontal arrows illustrate the sequencing strategy. Two consensus phosphorylation sites for cyclin-dependent kinases (cdk) are found in the amino terminal region of the protein and are indicated with light arrows pointing downwards. Two consensus sites potentially mediating destruction of the protein at specific stages of the cell cycle (ccb) are present toward the carboxyl terminus and are indicated with light arrows pointing upwards.

As described herein, vertebrate gene sequences that encode novel proteins closely related to proteins known to control DNA replication and entry into mitosis in fungi have been cloned and characterized. Specifically, vertebrate cdc6 genes have been identified which function in the regulation of DNA replication and entry of cells into mitosis. In a particular embodiment, the gene sequence is a human gene sequence (Hscdc6; previously referred to as human CSH gene, particularly in U.S. patent application Ser. No. 08/643,034, filed May 2, 1996, of which this application is a continuation-in-part application). In another embodiment, the gene sequence is a Xenopus laevis gene sequence (Xcdc6; previously referred to as a Xenopus CSH gene, particularly in U.S. patent application Ser. No. 08/643,034 filed May 2, 1996, of which this application is a continuation-in-part application).

The genes of the present invention are members of a family of genes which function in cell cycle regulation, particularly in the regulation of DNA replication and/or the control of the entry of the cell into mitosis. The present invention also relates to the polypeptides or proteins encoded by the genes described herein, as well as to antibodies which bind the subject polypeptides or proteins. In particular embodiments of the invention, genes which function in the regulation of DNA replication or entry of a cell into mitosis have the nucleotide sequence of SEQ ID NO: 1 or SEQ ID NO: 3, and the protein or polypeptide encoded by the genes described herein have the amino acid sequence of SEQ ID NO: 2 or SEQ ID NO: 4.

Cell Cycle Regulation

A particularly critical step in the cell cycle involves the decision to replicate DNA. In eukaryotic cells, the initiation of DNA replication has been studied most extensively in fungal species, particularly the budding and fission yeast, Saccharomyces cerevisiae and Schizosaccharomyces pombe, respectively. Less complete data acquired in insects, amphibians and humans suggest, however, that the fundamental mechanisms, and many of the proteins, involved in this process are similar in all eukaryotes (Sherr, Cell 79:551–555 (1994); Nigg, BioEssays 17:471 (1995)).

DNA replication is initiated from discrete locations within chromosomes by recruitment of an extensive set of proteins collectively termed the replication machinery (Stillman, J. Biol. Chem. 269:7047–7050 (1994a); Stillman, Cell 78:725–728 (1994b)). This process is best understood at present from studies on the yeast S. cerevisiae and S. pombe (Diffley, Current Opinions in Cell Biology 6:368–372 (1994); Rowley et al., Biochimica et Biophysica Acta 1217:239–256 (1994); Stillman (1994a); Stillman (1994b)). Replication origins in S. cerevisiae and S. pombe consist of specific DNA sequences (replicators) that are bound by nuclear proteins to provide the framework on which the other components of the replication machinery are assembled (Marahrens and Stillman, Science 255:817–823 (1992); Dubey et al., EMBO 13:3638–3647 (1994); Marahrens and Stillman, EMBO 13:3395–3400 (1994); Newlon and Theis, Current Opinions in Genetics and Development 3:752–758 (1994); Rao et al., Mol. Cell Biol. 14:7643–7651 (1994); Theis and Newlon, Mol. Cell Biol. 14:7652–7659 (1994); Clyne and Kelly, EMBO 14:6348–6357 (1995); Rao and Stillman, PNAS 92:2224–2228 (1995); Rowley et al., EMBO 14:2631–2641 (1995); Huang and Kowalski, Nucleic Acids Research 24:816–823 (1996)).

In S. cerevisiae, a multi-subunit complex known as ORC (origin Recognition Complex) binds to replicator sites within chromosomes (Bell and Stillman, Nature 357:128–134 (1992); Diffley and Cocker, Nature 357:169 (1992); Bell et al., Science 262:1844–1870 (1993); Li and Herskowitz, Science 262:1870–1874 (1993); Micklem et al., Nature 366:87–89 (1993); Diffley et al., Cell 78:303–316 (1994); Bell et al., Cell 83:563 (1995); Liang et al., Cell 81:667–676 (1995); Loo et al., Mol. Cell Biol. 6:741–756 (1995); Rao and Stillman (1995); Rowley et al. (1995)). ORC consists of six essential protein subunits (Palmer et al., Genetics 125:763–774 (1990); Bell and Stillman (1992); Bell et al. (1995)), and at least some of them are found in other eukaryotic species (Ehrenhofer-Murray et al., Science 270:1671–1674 (1995); Gavin et al., Science 270:1667–1671 (1995); Gossen et al., Science 270:1674–1677 (1995); Muzi-Falconi and Kelly, PNAS 92:12475-12470 (1994); Carpenter et al., Nature 379:357 (1996)). Binding of ORC to replicator DNA sequences in vivo can be detected by footprinting techniques, and it appears that ORC is bound to the chromosomes throughout the cell cycle, but the pattern of nuclease digestion changes (Diffley and Cocker (1992); Diffley et al. (1994); Rowley et al. (1994); Dahmann et al., Current Biology 5:1257 (1995); Diffley, Yeast 11:1651–1670 (1995); Cocker et al., Nature 379:180 (1996)). This is consistent with the viewpoint that other factors interact with ORC to trigger the initiation of replication at the G1/S phase boundary.

In budding yeasts this triggering function resides, at least in part, in a protein called cdc6p (Hartwell, J. Cell Biol. 15:803–817 (1976); Lisziewicz et al., Nucleic Acids Research 16:11507–11520 (1988); Zhou et al., J. Biol. Chem. 264:9022–9029 (1989); Palmer et al., Genetics 125:763–774 (1990); Bueno and Russell, EMBO 11:2167–2176 (1992); Hogan and Koshland, PNAS 89:3098–3102 (1992); Zwerschke et al., J. Biol. Chem. 269:23351–23356 (1994); Liang et al. (1995); Piatti et al., EMBO 1141:3788–3799 (1995); Bruschi et al., Mol. Genet. 249:8–18 (1996); Cocker et al. (1996)). Fission yeasts contain a closely related protein, cdc18, that appears to have a similar function (Kelly et al., *Cell* 74:371–382 (1993a); Kelly et al., *Cold Spring Harbor Symp Quant. Biol.* 58:637–644 (1993b); Nishitani and Nurse, *Cell* 83:397–405 (1995); Jallepalli and Kelly, *Genes and Development* 10:541–552 (1996); Leatherwood et al., *Nature* 379:360 (1996); Muzi-Falconi et al., *PNAS* 93:1566–1570 (1996)). Extensive evidence, acquired from genetic and biochemical studies, supports the viewpoint that cdc6p/cdc18 proteins have a unique and important role in the initiation of DNA replication.

The CDC6 gene was cloned by several labs by complementation of a mutation causing a cell-division-cycle-specific growth arrest in *S. cerevisiae* (Hartwell (1976); Lisziewicz et al. (1988); Zhou et al. (1989); Bueno and Russell (1992)). The sequence of the largest subunit of ORC, the orc1p, is highly related to the sequences of the cdc6p/cdc18 proteins, particularly in and around a putative purine nucleotide binding motif (Bell et al. (1995)). Yeast strains bearing null mutations in CDC6 are nonviable, and strains bearing temperature sensitive mutations in CDC6 suffer growth arrest with partially unreplicated DNA at the restrictive temperature (Lisziewicz et al. (1988); Zhou et al. (1989); Bueno and Russell (1992); Liang et al. (1995)). Even at temperatures permissive for viability, the frequency at which DNA replication is initiated from specific replicators is reduced in strains with CDC6 mutations (Liang et al. (1995); Piatti et al. (1995)). This phenotype can be reversed if multiple replicator sequences are located on the plasmid that is under selection (Hogan and Koshland (1992)).

Interestingly, over-expression of cdc18 protein results in repeated rounds of DNA replication in the absence of mitosis, such that cells accumulate concentrations of DNA greater than a 2N DNA content (normal for diploid cells) (Nishitani and Nurse (1995); Jallepalli and Kelly (1996); Leatherwood et al. (1996)). A similar abnormality is a common defect in human cancer cells. In contrast, under-expression of cdc6p/cdc18 proteins causes under-replication of the genome and abnormal entry into mitosis (Kelly et al. (1993a) and (1993b); Liang et al. (1995); Piatti et al. (1995); Muzi-Falconi et al. (1996)). The abundance of functional cdc6p/cdc18 proteins appears, therefore, to be rate-limiting for initiation of DNA replication at individual replicators.

CDC6 and cdc18+ genes are expressed at specific stages of the cell cycle (Kelly et al. (1993a); Zwerschke et al. (1994); Piatti et al. (1995); Muzi-Falconi et al. (1996)). Expression of mRNA encoding cdc6p peaks at the end of M phase in rapidly cycling *S. cerevisiae* cells, but a second peak of expression is evident in G1 if G1 is prolonged (Zwerschke et al. (1994); Piatti et al. (1995)). In contrast, the cdc18+ gene is expressed only at the G1 to S phase transition (Kelly et al. (1993a)). Both of these proteins are very unstable; the half life of cdc18 protein and cdc6p has been estimated as 5 minutes or less (piatti et al. (1995); Jallepalli and Kelly (1996); Muzi-Falconi et al. (1996)). Concentrations of cdc18 protein peak at the G1/S boundary and decline during late S phase, consistent with a role in triggering DNA replication. A requirement for renewed synthesis of cdc6p/cdc18 proteins is an important component of the mechanism that ensures that each segment of chromosomal DNA is replicated once, and only once, in each cell cycle.

Cdc6p and cdc18 proteins are rate limiting for replication initiation and have additional regulatory functions in controlling subsequent progression through the cell cycle. A deficiency in functional cdc6p/cdc18 protein causes mitosis in the absence of DNA replication (reductional anaphase) (Kelly et al. (1993a); Piatti et al. (1995)), leading to cell death. Conversely, overexpression of cdc18 protein stimulates additional rounds of DNA replication in the absence of mitosis, promoting polyploidy (Nishitani and Nurse (1995)). Thus, a decline in the concentration of cdc6p/cdc18 protein after the initiation of DNA replication appears to be necessary to release checkpoint controls and permit entry into mitosis (Bueno and Russell (1992)). The abundance of cdc18 protein is down-regulated by the activity of mitotic cyclins and cyclin-dependent kinase activity, and up-regulated by cyclin-dependent kinase (CDK) inhibitors such as rum1 protein (Jallepalli and Kelly (1996)).

Cdc6p demonstrates both functional and physical interactions with ORC protein subunits that bind to origins of DNA replication (Li and Herskowitz (1993); Liang et al. (1995)). Concomitant expression of temperature-sensitive mutant forms of cdc6p and either Orc2p or Orc5p is lethal at temperatures permissive for strains bearing only single mutations (synthetic lethality) (Liang et al. (1995)). Conversely, high concentrations of cdc6p generated from multicopy plasmids can rescue DNA replication at non-permissive temperatures in yeast strains bearing temperature-sensitive mutations in the Orc5p gene. Furthermore, cdc6p is present in protein complexes immunoprecipitated from yeast nuclear protein extracts with monoclonal antibodies directed against ORC subunits (Liang et al. (1995)). It also appears that the *S. pombe* cdc18 protein may interact with ORC (Leatherwood et al. (1996)). Evidence suggests that the cdc6p protein may be an ATPase (Zweschke et al. (1994)). The putative purine nucleotide binding motif in the cdc6p is essential for viability in yeast (M. Weinreich and B. Stillman, unpublished data). In concert, these data establish an important role for cdc6p/cdc18 proteins in the initiation of DNA replication and in the progression of cells into mitosis when DNA replication is complete.

Cloning of Xcdc6 and Hscdc6

The amino acid sequences of the cdc6p and cdc18 proteins were aligned, along with those of human and yeast ORC1 proteins previously described (Bell et al. (1995); Gavin et al. (1995)). ORC1 proteins contain several regions closely related to cdc6p/cdc18, including a putative nucleotide binding/ATPase domain, but are otherwise dissimilar (Gavin et al. (1995)). Certain regions that are conserved between the cdc6p and cdc18 proteins are not present in any of the ORC1 proteins. Based on these sequences, six degenerate oligonucleotide primers for the polymerase chain reaction (PCR) were designed, using blocks of 6 or 7 amino acids that were identical, or nearly so, in cdc6p and cdc18, but differed in two or more codons from sequences conserved among ORC1 proteins from *H. sapiens, K. lactis, S. pombe* and *S. cerevisiae*. This was important to avoid re-isolation of human ORC1 cDNA. The nucleotide sequence of each oligonucleotide primer was biased to reflect human usage codon probabilities. The design of primers that proved successful in amplifying partial Xenopus and human cDNA sequences from genes encoding Xcdc6 and Hscdc6 proteins is shown in FIG. 1. The primers were degenerate in the positions shown, and inosine (I) bases were included at positions of highest degeneracy in the predicted nucleotide sequence.

All six primers were tested in all possible combinations in polymerase chain reactions using cDNA prepared from human, amphibian or insect cells as the template. Amphibian and insect embryo mRNAs were used to make cDNA for this purpose because it was proposed that the embryo might store large amounts of the CDC6-related mRNA for the rapid rounds of cell division that occur in these organisms (Alberts et al. (1989)). A wide variety of reaction conditions were tested with a variety of template DNAs. The conditions that proved successful included 67 mM Tris HCl (pH 8.8), 16.6 mM ammonium sulfate, 10% dimethylsulfoxide, 6.7 mM EDTA, 8 mM magnesium chloride, 10 mM β-mercaptoethanol, 50 pmol of each oligonucleotide primer, 10 ng of DNA template, and 1 unit Taq polymerase in a total reaction volume of 25 μl. Conditions for PCR (29 cycles) included denaturation of DNA for 2 minutes (first cycle) or 40 seconds (subsequent cycles) at 94° C., primer annealing at 42° C. for 1 minute, and primer extension for 1 minute (cycles 1–28) or 5 minutes (cycle 29) at 72° C. Amplified products were purified after agarose gel electrophoresis and cloned into a plasmid vector (pCRII; Gahm et al., *PNAS U.S.A.* 88:10267–10271 (1991)). Complementary DNA inserts were sequenced from purified plasmid DNA using dideoxynucleotide chain termination chemistry (Sanger et al., *PNAS U.S.A.* 74:5463–5467 (1977)).

The most abundant PCR product identified from this screen was obtained using cDNA prepared from mRNA isolated from Xenopus oocytes as templates. The amplified product of 378 nucleotides encoded a predicted amino acid sequence with greater similarity to cdc6p/cdc18 than to ORC1 proteins. Using the same Xenopus oocyte cDNA as template, additional PCR was performed using 5' and 3' rapid amplification of cDNA ends (RACE) techniques, which yielded additional Xenopus cDNA segments that included all of the segments conserved in the comparison of cdc6p and cdc18 proteins. The cloned Xenopus cDNA includes the initiation codon, but does not extend to the authentic 3' terminus of the coding sequence.

Based on the sequence of the Xenopus cdc6p-related protein, new sets of non-degenerate oligonucleotide primers were synthesized using regions conserved between the predicted Xenopus protein, cdc6p and cdc18. Further rounds of PCR were performed using cDNA reverse-transcribed from RNA isolated from human cells as the template. One of these new primers, containing the sequence 5'-CCTCTCAGCCCCAGGAAACG-3' (SEQ ID NO: 5) in combination with degenerate primers from the original set based on Box 1 or Box 3 (FIG. 1) generated amplification products of 459 and 687 nucleotides, respectively. The predicted amino acid sequence encoded within these segments exhibited greater similarity to cdc6p and cdc18 than to ORC1 proteins and was greater than 90% identical to the amino acid sequence of the predicted Xenopus protein.

The larger (687 nt) fragment of Hscdc6 cDNA obtained by PCR amplification was radiolabeled and used as the probe for screening a human cDNA library carried in bacteriophage lambda phage gt10. In the first round of screening of 900,000 phage plaques, 18 clones were positive in duplicate lifts. Of these 18, 5 clones were positive in duplicate in a second round of screening. Each of theses 5 clones was isolated following a third round of plaque purification after plating at low density. Phage DNA was purified and characterized by PCR and restriction digests. cDNA inserts were isolated and cloned into a plasmid vector for sequencing. Plasmid clones isolated from the human cDNA library and used to determine the complete nucleotide sequence of Hscdc6 are illustrated schematically in FIG. 2.

The human cDNA encoding Hscdc6 includes an open reading frame of 1680 nucleotides, encoding a protein of 560 amino acids. The most upstream ATG, representing the putative initiation codon, is flanked by an in-frame stop codon in the 5' untranslated region (UTR). The termination codon of this open reading frame is flanked by multiple in-frame stop codons in the 3' UTR, 763 bases of which were included in the largest cDNA clone isolated from the phage library. Five overlapping segments of this cDNA were cloned into plasmid vectors for sequencing (pH7, pML, pH4, pL20 and pM8-8). Nucleotides 1 through 210 and 1891 through 2653 are non-coding regions of the gene and are useful, for example, as probes.

In addition, a match to a human expressed sequence tag was identified in the National Center for Biotechnology Information database. The sequenced region identified in the EST database represents only the region corresponding to amino acids 36–165 of Hscdc6. This region does not have sufficient identity to cdc6p or cdc18 to be identified without the additional sequence data obtained by cloning the partial Xenopus cDNA. Complete sequencing of the human cDNA clone bearing this tag (EST pT83032) and comparison to the sequence determined from the clones isolated directly from human cDNA showed that it represents a partial cDNA encoding amino acids 36–555 of Hscdc6.

Other landmarks identified in the Hscdc6 sequence are shown in the lower portion of FIG. 2. The box labeled CSB indicates the region containing conserved sequence blocks shared with yeast cdc6p and cdc18 and ORC1 proteins. Two consensus phosphorylation sites for cyclin-dependent kinases (cdk) (Jans et al., *JBC* 270:17064–17067 (1995)) are found in the amino terminal region of the protein and are indicated with light arrows pointing downwards. Two consensus sites potentially mediating destruction of the protein at specific stages of the cell cycle (ccb) (Amon et al., *Cell* 77:1037–1050 (1994)) are present toward the carboxyl terminus and are indicated with light arrows pointing upwards. A potential leucine zipper (zip) overlaps with conserved sequence block 4. The 5' UTR includes two consensus sites for DNA binding of SV40 T antigen (T Ag) (SenGupta and Borowiec, *EMBO* 4 (1994)), and an Alu repeat sequence (Alu element) is found within the 3' UTR.

Figure 4A:
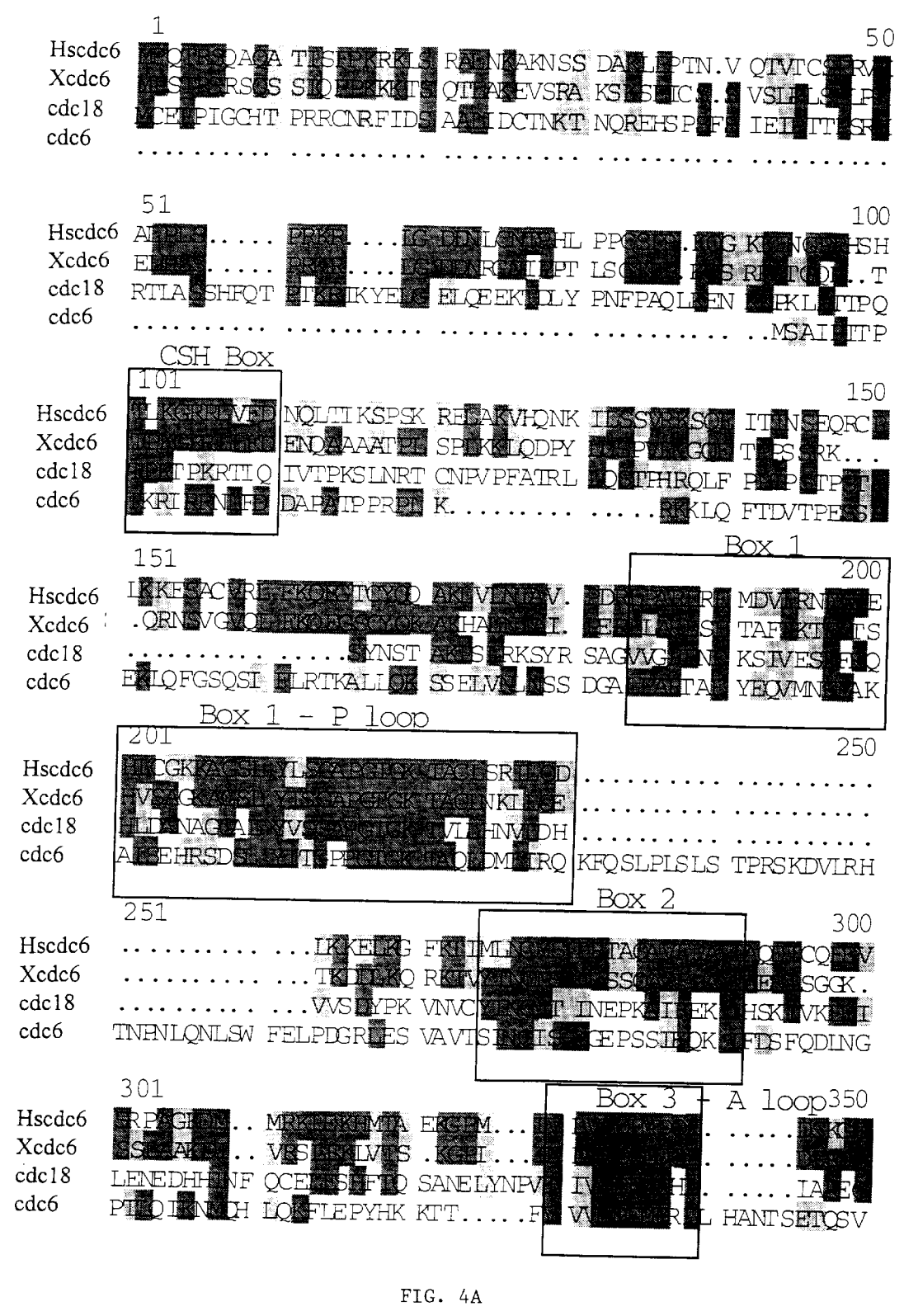
Figure 4B:
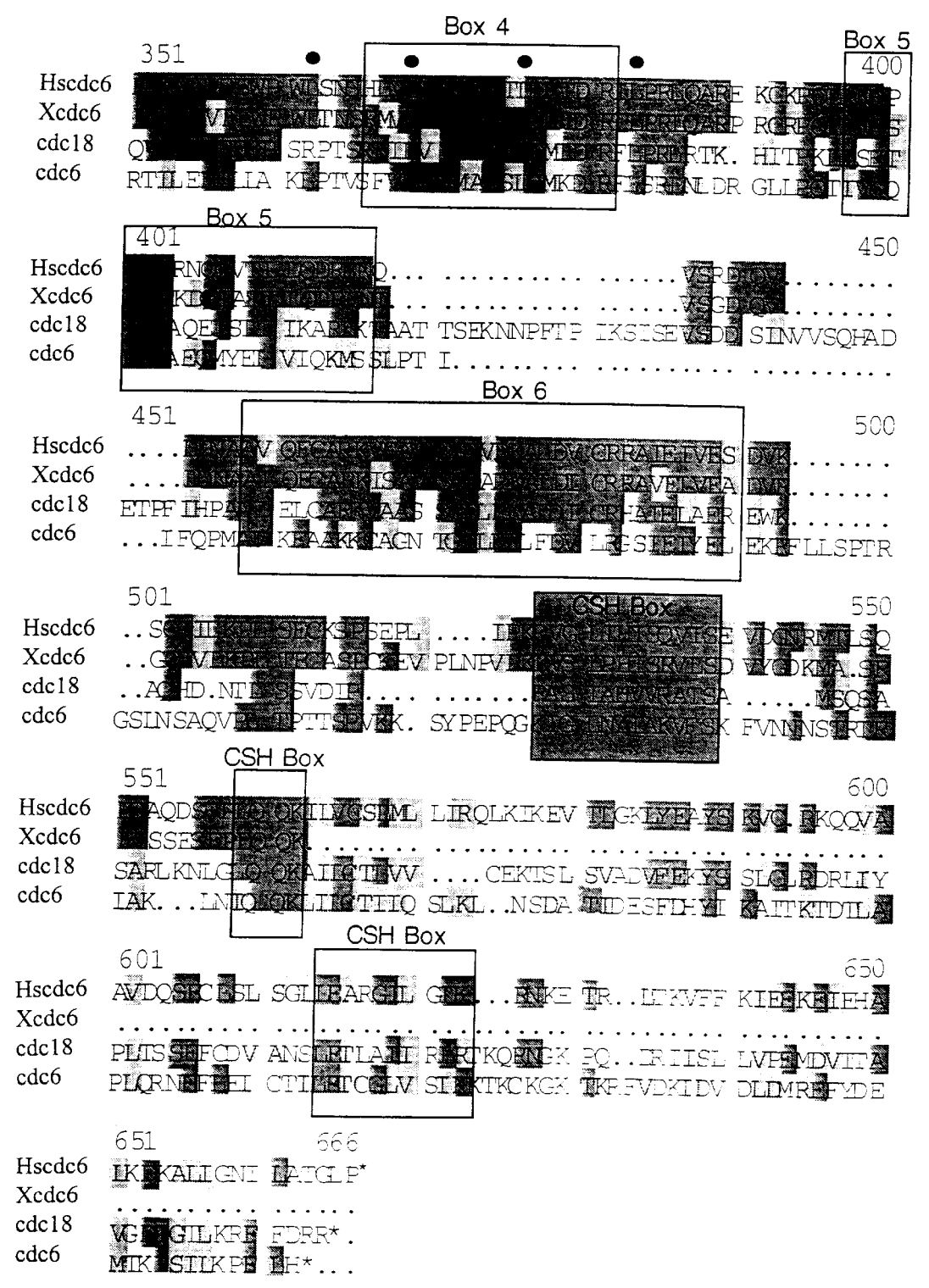

The complete nucleotide sequence of human Hscdc6 cDNA is shown in FIGS. 3A and 3B and 3C (SEQ ID NO: 1), and the partial nucleotide sequence of Xcdc6 cDNA is shown in FIGS. 6A and 6B (SEQ ID NO: 3). The predicted amino acid sequences are also shown (SEQ ID NOS: 2 and 4, respectively), and the alignment of these amino acid sequences with the fungal cdc6p/cdc18 proteins is shown in FIGS. 4A and 4B.

The present invention also relates to genes which function in the regulation of DNA replication or the entry of a cell into mitosis and which have a nucleotide sequence which hybridizes under conditions of medium stringency to a DNA sequence of SEQ ID NO: 1 or SEQ ID NO: 3. Stringency conditions which are appropriately termed "medium stringency" are known to those skilled in the art or can be found in standard texts, such as *Current Protocols in Molecular Biology*, John Wiley & Sons, N.Y. (1989), 6.3.1–6.3.6.

Figure 5:
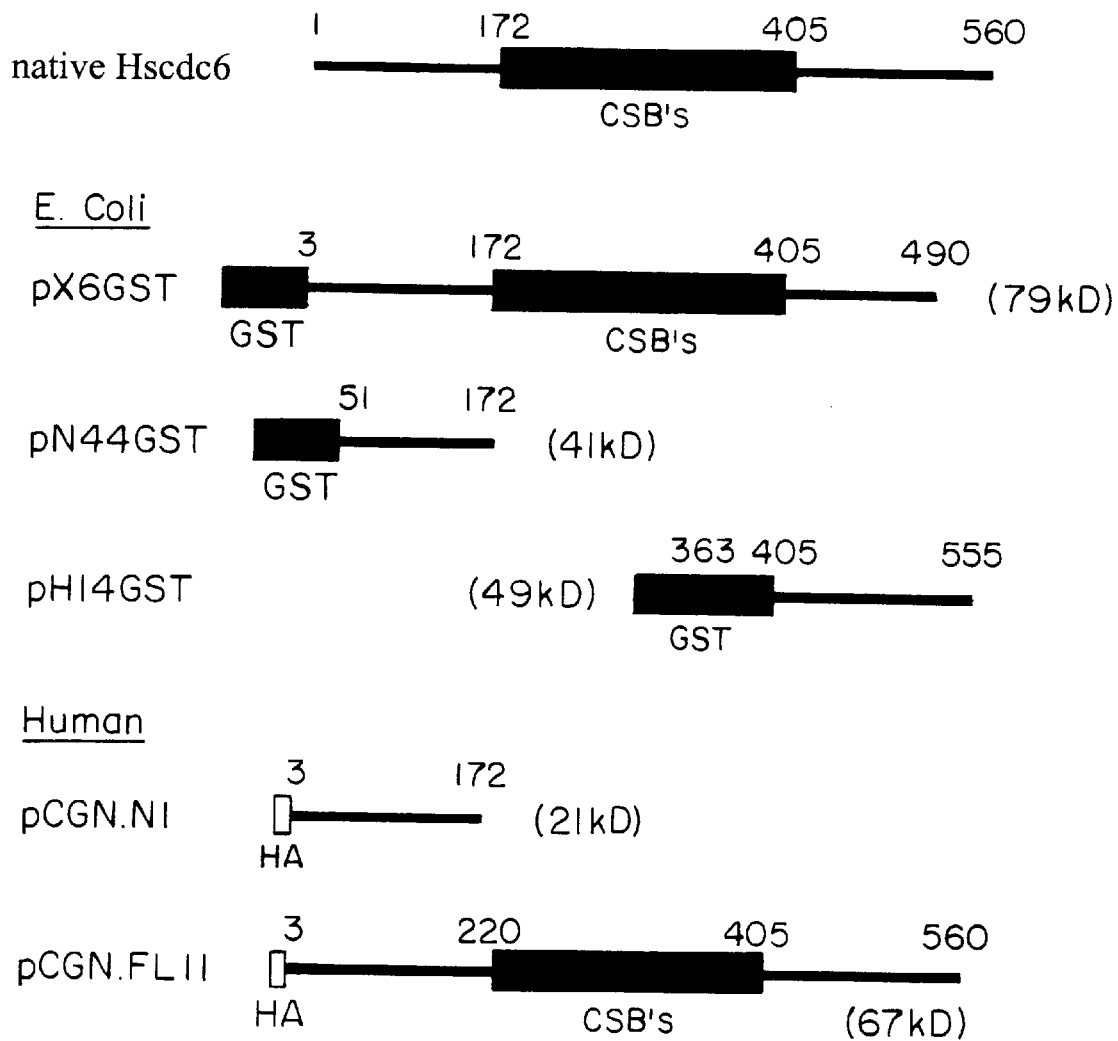
FIG. 5 illustrates plasmid constructions for expression of recombinant Hscdc6 in bacteria and in human cells.

Segments of Hscdc6 cDNA were engineered into plasmid vectors for expression of recombinant protein in bacteria and in human cells. The design of these expression plasmids is illustrated schematically in FIG. 5. Portions of Hscdc6 and Xcdc6 were expressed as GST fusion proteins under the control of the lac Z promoter in *E. coli,* and recombinant fusion proteins were purified by binding to glutathione-sepharose beads. Purified recombinant proteins were used to immunize rabbits to generate specific antibodies directed against Hscdc6 and Xcdc6. These antibodies recognize the recombinant protein expressed in *E. coli.*

Full-length or partial Hscdc6 cDNA sequences were also inserted into a mammalian vector in which expression of recombinant proteins is controlled by the major cytomegalovirus (CMV) immediate early promoter/enhancer, and the initiation codon is positioned so as to insert an influenza virus hemagglutinin antigen (HA) tag into the recombinant protein (Tanaka and Herr, *Cell* 60:375–386 (1990)).

The invention also provides additional expression vectors containing a nucleic acid sequence encoding a polypeptide of a Hscdc6 or Xcdc6 gene which is operably linked to at least one regulatory sequence. "Operably linked" is intended to mean that the nucleotide sequence is linked to a regulatory sequence in a manner which allows expression of the nucleic acid sequence. Regulatory sequences are art-recognized and are selected to produce a polypeptide which functions in the regulation of DNA replication and/or entry of the cell into mitosis. Accordingly, the term "regulatory sequence" includes promoters, enhancers, and other expression control elements which are described in Goeddel, *Gene Expression Technology: Methods in Enzymology* 185, Academic Press, San Diego, Calif. (1990). It should be understood that the design of the expression vector may depend on such factors as the choice of the host cell to be transformed and/or the type of protein desired to be expressed. For instance, the polypeptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17).

Prokaryotic and eukaryotic host cells transfected by the described vectors are also provided by this invention. For instance, cells which can be transfected with the vectors of the present invention include, but are not limited to, bacterial cells, such as *E. coli*, insect cells (baculovirus), yeast, and mammalian cells, such as Chinese hamster ovary cells (CHO).

Thus, a nucleotide sequence derived from the cloning of the Xcdc6 and Hscdc6 peptides and proteins described herein can be used to produce a recombinant form of the protein via prokaryotic or eukaryotic cellular processes. Ligating a polynucleotide sequence encoding Hscdc6 or Xcdc6 into a gene construct, such as an expression vector, and transforming or transfecting the gene construct containing the polynucleotide sequence into host cells, either eukaryotic (yeast, avian, insect or mammalian) or prokaryotic (bacterial cells), can be carried out using standard procedures (see for example, *Molecular Cloning: A Laboratory Manual*, 2nd Ed., ed. Sambrook et al. (Cold Spring Harbor Laboratory Press, 1989)). Similar procedures, or modifications thereof, can be employed to prepare recombinant proteins according to the present invention by microbial means or tissue-culture technology.

The present invention also relates to antibodies which bind a polypeptide or protein which functions in DNA replication or entry of a cell into mitosis. For instance, polyclonal and monoclonal antibodies which bind to the described polypeptide or protein are within the scope of the invention. A mammal, such as a mouse, hamster or rabbit, can be immunized with an immunogenic form of the polypeptide or protein (e.g., the entire protein or an antigenic fragment of the polypeptide or protein which is capable of eliciting an antibody response). Techniques for conferring immunogenicity on a protein or peptide which is itself not immunogenic include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained from the immunized animal, and if desired, polyclonal antibodies can be isolated from the serum. As described herein, purified recombinant proteins generated in *E. coli* were used to immunize rabbits to generate specific antibodies directed against Hscdc6. These antibodies recognize the recombinant protein expressed in *E. coli*. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 77–96 (1985)).

The Hscdc6 and Xcdc6 genes and peptides or proteins described herein permit the development of new biotechnological and pharmaceutical products to be used for the diagnosis and therapy of human cancers and other diseases associated with abnormal cellular proliferation. For example, the predicted role for Hscdc6 in the initiation of DNA replication, particularly the ability to control entry into both S phase and mitosis and to promote polyploidy when over-expressed, suggests that inherited or acquired mutations in the Hscdc6 protein, or in transcriptional control regions of the Hscdc6 gene that govern its expression, may contribute to the development of human cancers. Diagnostic tests which identify specific disease-related alleles or alteration of expression of the Hscdc6 gene in peripheral blood lymphocytes or in tumor material will improve the clinical management of patients at risk for the development of specific malignancies or of patients with established malignancies.

Disease-related alleles of Hscdc6 bearing specific DNA sequence alterations which are associated with particular conditions can be identified. As defined herein, "alteration" includes disruption of the gene (e.g., deletion of one or more nucleotides, addition of one or more nucleotides, or change in one or more nucleotides) and loss (deletion, either functional or physical) of the gene. The nucleotide sequences described herein, or their complements, are useful as hybridization probes or primers for an amplification method, such as polymerase chain reaction, to show the presence, absence or disruption of the genes of the present invention. Probes and primers can have all or a portion of the nucleic acid sequences of the genes described herein or all or a portion of their complements. The probes and primers can be any length, provided that they are of sufficient length and appropriate composition (i.e., appropriate nucleic acid sequence) to hybridize to all or an identifying or characteristic portion of the genes described herein or to a disrupted form of the genes, and remain hybridized under the conditions used.

Accordingly, by combining probes derived either from the isolated native sequence of the Hscdc6 gene or from the primers disclosed herein, with DNA from a sample obtained from an individual to be assessed, under conditions suitable for hybridization, it can be determined whether the sample from the individual contains the intact gene. Similarly, hybridization conditions can be selected such that the probes will hybridize only with altered DNA and not with unaltered (wild type or non-mutant) sequences; that is, the probes can be designed to recognize only particular alterations in the nucleic acid sequence of the gene, including addition of one or more nucleotides, deletion of one or more nucleotides or change in one or more nucleotides (including substitution of one or more nucleotides for nucleotides normally present in the sequence).

Alternatively, disorders affecting the peripheral blood lymphocytes or associated with tumors can result from altered expression of the genes described herein. For example, particular disorders may be associated with increased expression or decreased expression (including reduction of expression or complete absence) of the Hscdc6 gene relative to expression of Hscdc6 independent of the disorder. A different expression pattern, e.g., expression of Hscdc6 at times and/or locations at which Hscdc6 is not usually expressed or absence of Hscdc6 expression at times and/or locations at which expression usually occurs, can also be associated with proliferative disorders. A difference in expression patterns can be identified by quantitative and/or qualitative comparison of Hscdc6 expression in individuals having or suspected of having a disorder associated with altered expression patterns and in individuals not having the disorder. Such an analysis can include comparison of the levels of gene expression or the timing and/or location of gene expression.

These differences in Hscdc6 nucleotide sequence or expression patterns between individuals having or suspected of having a disorder and individuals not having the disorder are useful as the basis for a method of diagnosing or aiding in the diagnosis of conditions associated with proliferative disorders. This method can also be used to predict the likelihood that an individual is at increased risk for a particular condition associated with abnormal cell proliferation. The present method has utility with respect to conditions which involve abnormal cell division or proliferation, such as cancers, including tumors and blood-based abnormalities (e.g., leukemias) and conditions which involve polyploidy. The invention also relates to compositions (e.g., oligonucleotides, antibodies, small molecules, proteins and polypeptides) useful in the method.

Accordingly, the invention pertains to a method of diagnosing a condition associated with alteration of Hscdc6, comprising the steps of obtaining a DNA sample from an individual to be assessed; processing the DNA sample such that the DNA is available for hybridization; combining the processed DNA with nucleic acid sequences complementary to the nucleotide sequence of SEQ ID NO: 1, under conditions appropriate for hybridization of the probes with complementary nucleic acid sequences in the DNA sample, thereby producing a combination; and detecting hybridization in the combination. Reduced hybridization (e.g., decrease in or absence of hybridization) in the combination, in comparison with an appropriate control sample, is indicative of a condition associated with alteration of Hscdc6.

Alternatively, the invention relates to a method of diagnosing a condition associated with alteration of Hscdc6, comprising the steps of obtaining a DNA sample from an individual to be assessed; processing the DNA sample such that the DNA is available for hybridization; combining the processed DNA with nucleic acid sequences complementary to the nucleotide sequence of SEQ ID NO: 1, under conditions appropriate for hybridization of the probes with altered complementary nucleic acid sequences in the DNA sample, but not with unaltered complementary nucleic acid sequences, thereby producing a combination; and detecting hybridization in the combination. Presence of hybridization (including increased hybridization in comparison with an appropriate control) in the combination is indicative of a condition associated with alteration of Hscdc6.

Forced expression in fungal cells of yeast proteins related to Hscdc6 and Xcdc6, such as cdc18, leads to DNA replication in the absence of mitosis, resulting in polyploidy. The development of polyploidy in human cells often represents a discrete step in the progression of benign or non-aggressive tumors into increasingly malignant forms. Thus, diagnostic tests to identify quantitative or qualitative abnormalities in Hscdc6 will aid clinicians in defining the prognosis and in tailoring the therapy for human cancer patients.

Hscdc6 also has unique potential as a target for drug- or gene-based therapies designed to slow the growth or promote destruction of human tumor cells. Therapeutic compositions can be targeted or delivered to appropriate cells in an individual utilizing a variety of known delivery or targeting vehicles, including but not limited to antibodies and liposomal compositions. The knowledge of the amino acid sequence of Hscdc6 proteins permits the identification of drugs that inhibit the function of Hscdc6, thereby blocking DNA replication and stopping the growth of human tumors. Inhibition of Hscdc6 would also drive cells with unreplicated DNA into mitosis, thereby causing cell death. This mechanism of action is unique and unlike that of drugs currently used to treat human cancers. Inhibitors of Hscdc6 function will block DNA replication at a step downstream of pathways triggered by growth factors, kinase cascades and proteins acting to regulate the cell cycle.

Accordingly, this invention pertains to a method of treating a tumor in an individual comprising administering an antagonist of Hscdc6 to an individual in a manner such that the antagonist enters the tumor cells. The antagonist inhibits the activity of the Hscdc6 gene or protein and causes at least one of two possible results: inhibition of tumor cell DNA replication, with concomitant inhibition of tumor growth, and mitotic division of tumor cells with unreplicated DNA, resulting in tumor cell death. As used herein, inhibition of tumor cell DNA replication includes decreasing the rate or frequency of DNA replication as well as completely preventing DNA replication. Also, as defined herein, inhibition of tumor growth, which results from tumor cell death, includes slowing the growth of the subject tumor, stopping the growth of the tumor and decreasing the size of the tumor. Antagonists of Hscdc6 include compositions which block or inhibit the function or activity of Hscdc6 or which decrease the expression or enhance or increase the down-regulation of Hscdc6, both at the DNA or RNA (nucleic acid) and protein (amino acid) levels. For instance, agonists of Hscdc6 include but are not limited to cyclin-dependent kinases, mitotic cyclins and Hscdc6 antisense molecules.

In addition, drugs or gene therapies that stabilize Hscdc6 or augment its function in the G2 and M phases of the cell cycle will block mitosis, even though DNA replication continues. Programmed cell death is a likely consequence of a Hscdc6-induced block to mitosis, and will inhibit tumor growth or promote tumor regression. Thus, drugs or gene-based therapies designed either to block the function of Hscdc6 or to augment its function have application to the therapy of human cancers. For example, the present invention pertains to a method of treating a tumor in an individual comprising administering Hscdc6 or an agonist of Hscdc6 to a the individual in such a manner that the Hscdc6 or Hscdc6 agonist enters the tumor cells. Introduction of Hscdc6 or and agonist of Hscdc6 to a cell in the G2 or M phase of the cell cycle prevents entry of the cell into mitosis and thus causes tumor cell death. As used herein, the term "agonist" of Hscdc6 is intended to mean a composition which mimics or enhances the function or activity of Hscdc6 or which prevents or inhibits the down-regulation or decrease in expression of Hscdc6, both at the DNA or RNA (nucleic acid) and protein (amino acid) levels. For instance, agonists of Hscdc6 include cyclin-dependent kinase inhibitors such as rum1. Prevention of cellular mitosis results in tumor cell death and inhibition of tumor growth.

In this context, drugs designed on the basis of the Hscdc6 protein sequence and intended for use in humans include small non-peptide molecules, peptides or proteins related to Hscdc6 or designed to alter the function of endogenous Hscdc6, or DNA or RNA sequences encoding proteins or peptides related to Hscdc6 or designed to alter the function of endogenous Hscdc6.

In a similar manner, knowledge of the Hscdc6 gene sequence can be used to develop novel methods and products for blocking cell proliferation in disorders other than cancer, including but not limited to, atherosclerotic vascular disease, vascular restenosis following medical or surgical reperfusion procedures, psoriasis, inflammatory arthritis and other inflammatory diseases, autoimmune diseases, and rejection of transplanted organs. Accordingly, the present invention provides a method of inhibiting undesirable cell proliferation in an individual comprising administering an agonist or antagonist of Hscdc6 to the individual in such a manner that the agonist or antagonist enters the cells in which it is desirable to inhibit proliferation. An antagonist of Hscdc6 will prevent or reduce the activity of Hscdc6, and thereby prevent the replication of cellular DNA; cells with unreplicated DNA will enter mitosis and cell death will result. An agonist of Hscdc6 will prolong or increase the effects of Hscdc6, resulting in polyploidy and preventing mitosis; cells which are affected in this manner will undergo programmed cell death.

In addition, the ability of Hscdc6 to initiate DNA replication can be exploited for the development of novel products to enhance cell proliferation for therapy of conditions associated with loss of viable tissue in an individual, including but not limited to, traumatic injury, myocardial infarction, cardiomyopathy, renal failure, hepatic failure and stroke. For example, this invention provides a method of enhancing cell proliferation for therapy of a condition associated with loss of viable tissue in an individual comprising administering Hscdc6 or an agonist of Hscdc6 to an individual such that it enters cells in the individual. The activity of Hscdc6 or an Hscdc6 agonist causes initiation of DNA replication in the cell and entry of the cell into mitosis. Administration of Hscdc6 or an Hscdc6 agonist can supplement, enhance or replace the natural-occurring levels of Hscdc6 and enhance cell proliferation.

Accordingly, the present invention also pertains to pharmaceutical compositions comprising a gene encoding a polypeptide or protein which functions in the regulation of DNA replication or entry of a cell into mitosis, or proteins or polypeptides encoded thereby, particularly an Hscdc6 protein or an Xcdc6 polypeptide. For instance, compositions of the present invention can be formulated with a physiologically acceptable medium or carrier to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of exogenous Hscdc6 or Xcdc6 polypeptides at the site of treatment include, but are not limited to, intradermal, intramuscular, intraperitoneal, intravenous, subcutaneous, oral and intranasal. Other suitable methods of introduction can also include rechargeable or biodegradable devices and slow release polymeric devices. Also encompassed by the present invention are pharmaceutical compositions comprising an agonist or antagonist of Hscdc6 or Xcdc6, including oligonucleotides, polypeptides, proteins and small molecules. The pharmaceutical compositions of this invention can also be administered as part of a combinatorial therapy with other agents.

The examples provided herein are offered for the purpose of illustrating the present invention only and are not to be construed to limit the scope of this invention. The teachings of all references cited herein are incorporated herein by reference.

Equivalents

Those skilled in the art will recognize, or be able to ascertain, using no more than routine experimentation, many equivalents to the specific embodiments of the invention described herein. Such equivalents are intended to be encompassed by the following claims:

We claim:

1. A method of inhibiting DNA replication in a tumor cell comprising introducing a Hscdc6 antagonist into the tumor cell, wherein Hscdc6 is inhibited, thereby inhibiting DNA replication.

2. The method of claim 1, wherein size of the tumor cell is reduced.

3. The method of claim 1, wherein rate or frequency of DNA replication is decreased.

4. A method of inhibiting tumor cell proliferation comprising introducing a Hscdc6 antagonist into a tumor cell, wherein Hscdc6 is inhibited, thereby inhibiting tumor cell proliferation.

5. The method of claim 4, wherein tumor cell proliferation ceases.

6. The method of claim 4, wherein tumor cell size is decreased.

7. A method of inhibiting tumor cell growth comprising introducing a Hscdc6 antagonist into a tumor cell, wherein Hscdc6 is inhibited, thereby inhibiting tumor cell growth.

8. The method of claim 7, wherein tumor cell growth ceases.

9. A method of inhibiting Hscdc6 expression in tumor cells comprising introducing a Hscdc6 antagonist into the tumor cells, wherein Hscdc6 expression is inhibited.

10. The method of claim 9, wherein the antagonist is selected from the group consisting of:

a cyclin dependent kinase and a Hscdc6 antisense molecule.

11. A method of inhibiting Hscdc6 protein activity comprising introducing into a tumor cell an antibody or antibody fragment that is specific to Hscdc6, wherein Hscdc6 protein activity is inhibited.

12. The method of claim 11, wherein the antibody or antibody fragment is a monoclonal or polyclonal antibody or fragment thereof.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 2774 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 219..1898

(xi) SEQUENCE DESCRIPTION: SEQ ID NO:1:

-continued

| | |
|---|---:|
| ACCCACTCGA GCGCGGCTGG AGTTTGCTGC TGCCGCTGTG CAGTTTGTTC AGGGGCTTGT | 60 |
| GGCGGTGAGT CCGAGAGGCT GCGTGTGAGA GACGTGAGAA GGATCCTGCA CTGAGGAGGT | 120 |
| GGAAAGAAGA GGATTGCTCG AGGAGGCCTG GGTCTGTGA GACAGCGGAG CTGGGTGAAG | 180 |
| GCTGCGGGTT CCGGCGAGGC CTGAGCTGTG CTGTCGTC ATG CCT CAA ACC CGA | 233 |
|                                                                       Met Pro Gln Thr Arg | |
|                                                                          1            5 | |
| TCC CAG GCA CAG GCT ACA ATC AGT TTT CCA AAA AGG AAG CTG TCT CGG | 281 |
| Ser Gln Ala Gln Ala Thr Ile Ser Phe Pro Lys Arg Lys Leu Ser Arg | |
|           10                       15                       20 | |
| GCA TTG AAC AAA GCT AAA AAC TCC AGT GAT GCC AAA CTA GAA CCA ACA | 329 |
| Ala Leu Asn Lys Ala Lys Asn Ser Ser Asp Ala Lys Leu Glu Pro Thr | |
|               25                     30                       35 | |
| AAT GTC CAA ACC GTA ACC TGT TCT CCT CGT GTA AAA GCC CTG CCT CTC | 377 |
| Asn Val Gln Thr Val Thr Cys Ser Pro Arg Val Lys Ala Leu Pro Leu | |
|       40                          45                       50 | |
| AGC CCC AGG AAA CGT CTG GGC GAT GAC AAC CTA TGC AAC ACT CCC CAT | 425 |
| Ser Pro Arg Lys Arg Leu Gly Asp Asp Asn Leu Cys Asn Thr Pro His | |
|      55                     60                     65 | |
| TTA CCT CCT TGT TCT CCA CCA AAG CAA GGC AAG AAA GAG AAT GGT CCC | 473 |
| Leu Pro Pro Cys Ser Pro Pro Lys Gln Gly Lys Lys Glu Asn Gly Pro | |
| 70                    75                     80                       85 | |
| CCT CAC TCA CAT ACA CTT AAG GGA CGA AGA TTG GTA TTT GAC AAT CAG | 521 |
| Pro His Ser His Thr Leu Lys Gly Arg Arg Leu Val Phe Asp Asn Gln | |
|                   90                     95                     100 | |
| CTG ACA ATT AAG TCT CCT AGC AAA AGA GAA CTA GCC AAA GTT CAC CAA | 569 |
| Leu Thr Ile Lys Ser Pro Ser Lys Arg Glu Leu Ala Lys Val His Gln | |
|               105                     110                   115 | |
| AAC AAA ATA CTT TCT TCA GTT AGA AAA AGT CAA GAG ATC ACA ACA AAT | 617 |
| Asn Lys Ile Leu Ser Ser Val Arg Lys Ser Gln Glu Ile Thr Thr Asn | |
|          120                     125                   130 | |
| TCT GAG CAG AGA TGT CCA CTG AAG AAA GAA TCT GCA TGT GTG AGA CTA | 665 |
| Ser Glu Gln Arg Cys Pro Leu Lys Lys Glu Ser Ala Cys Val Arg Leu | |
| 135                    140                     145 | |
| TTC AAG CAA GAA GGC ACT TGC TAC CAG CAA GCA AAG CTG GTC CTG AAC | 713 |
| Phe Lys Gln Glu Gly Thr Cys Tyr Gln Gln Ala Lys Leu Val Leu Asn | |
| 150                    155                     160                   165 | |
| ACA GCT GTC CCA GAT CGG CTG CCT GCC AGG GAA AGG GAG ATG GAT GTC | 761 |
| Thr Ala Val Pro Asp Arg Leu Pro Ala Arg Glu Arg Glu Met Asp Val | |
|               170                     175                   180 | |
| ATC AGG AAT TTC TTG AGG GAA CAC ATC TGT GGG AAA AAA GCT GGA AGC | 809 |
| Ile Arg Asn Phe Leu Arg Glu His Ile Cys Gly Lys Lys Ala Gly Ser | |
|                 185                     190                   195 | |
| CTT TAC CTT TCT GGT GCT CCT GGA ACT GGA AAA ACT GCC TGC TTA AGC | 857 |
| Leu Tyr Leu Ser Gly Ala Pro Gly Thr Gly Lys Thr Ala Cys Leu Ser | |
|          200                     205                   210 | |
| CGG ATT CTG CAA GAC CTC AAG AAG GAA CTG AAA GGC TTT AAA ACT ATC | 905 |
| Arg Ile Leu Gln Asp Leu Lys Lys Glu Leu Lys Gly Phe Lys Thr Ile | |
|      215                     220                     225 | |
| ATG CTG AAT TGC ATG TCC TTG AGG ACT GCC CAG GCT GTA TTC CCA GCT | 953 |
| Met Leu Asn Cys Met Ser Leu Arg Thr Ala Gln Ala Val Phe Pro Ala | |
| 230                    235                     240                   245 | |
| ATT GCT CAG GAG ATT TGT CAG GAA GAG GTA TCC AGG CCA GCT GGG AAG | 1001 |
| Ile Ala Gln Glu Ile Cys Gln Glu Glu Val Ser Arg Pro Ala Gly Lys | |
|                 250                     255                   260 | |
| GAC ATG ATG AGG AAA TTG GAA AAA CAT ATG ACT GCA GAG AAG GGC CCC | 1049 |
| Asp Met Met Arg Lys Leu Glu Lys His Met Thr Ala Glu Lys Gly Pro | |
|          265                     270                   275 | |

```
ATG ATT GTG TTG GTA TTG GAC GAG ATG GAT CAA CTG GAC AGC AAA GGC         1097
Met Ile Val Leu Val Leu Asp Glu Met Asp Gln Leu Asp Ser Lys Gly
            280             285             290

CAG GAT GTA TTG TAC ACG CTA TTT GAA TGG CCA TGG CTA AGC AAT TCT         1145
Gln Asp Val Leu Tyr Thr Leu Phe Glu Trp Pro Trp Leu Ser Asn Ser
    295             300             305

CAC TTG GTG CTG ATT GGT ATT GCT AAT ACC CTG GAT CTC ACA GAT AGA         1193
His Leu Val Leu Ile Gly Ile Ala Asn Thr Leu Asp Leu Thr Asp Arg
310             315             320             325

ATT CTA CCT AGG CTT CAA GCT AGA GAA AAA TGT AAG CCA CAG CTG TTG         1241
Ile Leu Pro Arg Leu Gln Ala Arg Glu Lys Cys Lys Pro Gln Leu Leu
                330             335             340

AAC TTC CCA CCT TAT ACC AGA AAT CAG ATA GTC ACT ATT TTG CAA GAT         1289
Asn Phe Pro Pro Tyr Thr Arg Asn Gln Ile Val Thr Ile Leu Gln Asp
            345             350             355

CGA CTT AAT CAG GTA TCT AGA GAT CAG GTT CTG GAC AAT GCT GCA GTT         1337
Arg Leu Asn Gln Val Ser Arg Asp Gln Val Leu Asp Asn Ala Ala Val
    360             365             370

CAA TTC TGT GCC CGC AAA GTC TCT GCT GTT TCA GGA GAT GTT CGC AAA         1385
Gln Phe Cys Ala Arg Lys Val Ser Ala Val Ser Gly Asp Val Arg Lys
375             380             385

GCA CTG GAT GTT TGC AGG AGA GCT ATT GAA ATT GTA GAG TCA GAT GTC         1433
Ala Leu Asp Val Cys Arg Arg Ala Ile Glu Ile Val Glu Ser Asp Val
390             395             400             405

AAA AGC CAG ACT ATT CTC AAA CCA CTG TCT GAA TGT AAA TCA CCT TCT         1481
Lys Ser Gln Thr Ile Leu Lys Pro Leu Ser Glu Cys Lys Ser Pro Ser
                410             415             420

GAG CCT CTG ATT CCC AAG AGG GTT GGT CTT ATT CAC ATA TCC CAA GTC         1529
Glu Pro Leu Ile Pro Lys Arg Val Gly Leu Ile His Ile Ser Gln Val
            425             430             435

ATC TCA GAA GTT GAT GGT AAC AGG ATG ACC TTG AGC CAA GAG GGA GCA         1577
Ile Ser Glu Val Asp Gly Asn Arg Met Thr Leu Ser Gln Glu Gly Ala
    440             445             450

CAA GAT TCC TTC CCT CTT CAG CAG AAG ATC TTG GTT TGC TCT TTG ATG         1625
Gln Asp Ser Phe Pro Leu Gln Gln Lys Ile Leu Val Cys Ser Leu Met
455             460             465

CTC TTG ATC AGG CAG TTG AAA ATC AAA GAG GTC ACT CTG GGG AAG TTA         1673
Leu Leu Ile Arg Gln Leu Lys Ile Lys Glu Val Thr Leu Gly Lys Leu
470             475             480             485

TAT GAA GCC TAC AGT AAA GTC TGT CGC AAA CAG CAG GTG GCG GCT GTG         1721
Tyr Glu Ala Tyr Ser Lys Val Cys Arg Lys Gln Gln Val Ala Ala Val
                490             495             500

GAC CAG TCA GAG TGT TTG TCA CTT TCA GGG CTC TTG GAA GCC AGG GGC         1769
Asp Gln Ser Glu Cys Leu Ser Leu Ser Gly Leu Leu Glu Ala Arg Gly
            505             510             515

ATT TTA GGA TTA AAG AGA AAC AAG GAA ACC CGT TTG ACA AAG GTG TTT         1817
Ile Leu Gly Leu Lys Arg Asn Lys Glu Thr Arg Leu Thr Lys Val Phe
    520             525             530

TTC AAG ATT GAA GAG AAA GAA ATA GAA CAT GCT CTG AAA GAT AAA GCT         1865
Phe Lys Ile Glu Glu Lys Glu Ile Glu His Ala Leu Lys Asp Lys Ala
535             540             545

TTA ATT GGA AAT ATC TTA GCT ACT GGA TTG CCT TAAATTCTTC TCTTACACCC      1918
Leu Ile Gly Asn Ile Leu Ala Thr Gly Leu Pro
550             555             560

CACCCGAAAG TATTCAGCTG GCATTTAGAG AGCTACAGTC TTCATTTTAG TGCTTTACAC      1978

ATTCGGGCCT GAAAACAAAT ATGACCTTTT TTACTTGAAG CCAATGAATT TTAATCTATA      2038

GATTCTTTAA TATTAGCACA GAATAATATC TTTGGGTCTT ACTATTTTTA CCCATAAAAG      2098

TGACCAGGTA GACCCTTTTT AATTACATTC ACTACTTCTA CCACTTGTGT ATCTCTAGCC      2158
```

```
AATGTGCTTG CAAGTGTACA GATCTGTGTA GAGGAATGTG TGTATATTTA CCTCTTCGTT    2218

TGCTCAAACA TGAGTGGGTA TTTTTTTGTT TGTTTTTTTT GTTGTTGTTG TTTTTGAGGC    2278

GCGTCTCACC CTGTTGCCCA GGCTGGAGTG CAATGGCGCG TTCTCTGCTC ACTACAGCAC    2338

CCGCTTCCCA GGTTGAAGTG ATTCTCTTGC CTCAGCCTCC CGAGTAGCTG GGATTACAGG    2398

TGCCCACCAC CGCGCCCAGC TAATTTTTTA ATTTTTAGTA GAGACAGGGT TTTACCATGT    2458

TGGCCAGGCT GGTCTTGAAC TCCTGACCCT CAAGTGATCT GCCCACCTTG GCCTCCCTAA    2518

GTGCTGGGAT TATAGGCGTG AGCCACCATG CTCAGCCATT AAGGTATTTT GTTAAGAACT    2578

TTAAGTTTAG GGTAAGAAGA ATGAAAATGA TCCAGAAAAA TGCAAGCAAG TCCACATGGA    2638

GATTTGGAGG ACACTGGTTA AAGACCAACC TAATAAATTT CAGCTCGGTG TATTCACGTC    2698

ATAACGAGGA GTGTACGTCT AAAACAGTAG GTGATTACTT AACAGACATC GGTTGACTGA    2758

CAACGAGGTT AAGATG                                                    2774
```

(2) INFORMATION FOR SEQ ID NO:2:

(i) SEQUENCE CHARACTERISTICS:
        (A) LENGTH: 560 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Gln Thr Arg Ser Gln Ala Gln Ala Thr Ile Ser Phe Pro Lys
 1               5                  10                  15

Arg Lys Leu Ser Arg Ala Leu Asn Lys Ala Lys Asn Ser Ser Asp Ala
            20                  25                  30

Lys Leu Glu Pro Thr Asn Val Gln Thr Val Thr Cys Ser Pro Arg Val
        35                  40                  45

Lys Ala Leu Pro Leu Ser Pro Arg Lys Arg Leu Gly Asp Asp Asn Leu
    50                  55                  60

Cys Asn Thr Pro His Leu Pro Pro Cys Ser Pro Lys Gln Gly Lys
65                  70                  75                  80

Lys Glu Asn Gly Pro Pro His Ser His Thr Leu Lys Gly Arg Arg Leu
                85                  90                  95

Val Phe Asp Asn Gln Leu Thr Ile Lys Ser Pro Ser Lys Arg Glu Leu
            100                 105                 110

Ala Lys Val His Gln Asn Lys Ile Leu Ser Ser Val Arg Lys Ser Gln
        115                 120                 125

Glu Ile Thr Thr Asn Ser Glu Gln Arg Cys Pro Leu Lys Lys Glu Ser
    130                 135                 140

Ala Cys Val Arg Leu Phe Lys Gln Glu Gly Thr Cys Tyr Gln Gln Ala
145                 150                 155                 160

Lys Leu Val Leu Asn Thr Ala Val Pro Asp Arg Leu Pro Ala Arg Glu
                165                 170                 175

Arg Glu Met Asp Val Ile Arg Asn Phe Leu Arg Glu His Ile Cys Gly
            180                 185                 190

Lys Lys Ala Gly Ser Leu Tyr Leu Ser Gly Ala Pro Gly Thr Gly Lys
        195                 200                 205

Thr Ala Cys Leu Ser Arg Ile Leu Gln Asp Leu Lys Lys Glu Leu Lys
    210                 215                 220

Gly Phe Lys Thr Ile Met Leu Asn Cys Met Ser Leu Arg Thr Ala Gln
225                 230                 235                 240
```

```
Ala Val Phe Pro Ala Ile Ala Gln Glu Ile Cys Gln Glu Glu Val Ser
                245                 250                 255

Arg Pro Ala Gly Lys Asp Met Met Arg Lys Leu Glu Lys His Met Thr
            260                 265                 270

Ala Glu Lys Gly Pro Met Ile Val Leu Val Leu Asp Glu Met Asp Gln
        275                 280                 285

Leu Asp Ser Lys Gly Gln Asp Val Leu Tyr Thr Leu Phe Glu Trp Pro
    290                 295                 300

Trp Leu Ser Asn Ser His Leu Val Leu Ile Gly Ile Ala Asn Thr Leu
305                 310                 315                 320

Asp Leu Thr Asp Arg Ile Leu Pro Arg Leu Gln Ala Arg Glu Lys Cys
                325                 330                 335

Lys Pro Gln Leu Leu Asn Phe Pro Pro Tyr Thr Arg Asn Gln Ile Val
            340                 345                 350

Thr Ile Leu Gln Asp Arg Leu Asn Gln Val Ser Arg Asp Gln Val Leu
        355                 360                 365

Asp Asn Ala Ala Val Gln Phe Cys Ala Arg Lys Val Ser Ala Val Ser
    370                 375                 380

Gly Asp Val Arg Lys Ala Leu Asp Val Cys Arg Arg Ala Ile Glu Ile
385                 390                 395                 400

Val Glu Ser Asp Val Lys Ser Gln Thr Ile Leu Lys Pro Leu Ser Glu
                405                 410                 415

Cys Lys Ser Pro Ser Glu Pro Leu Ile Pro Lys Arg Val Gly Leu Ile
            420                 425                 430

His Ile Ser Gln Val Ile Ser Glu Val Asp Gly Asn Arg Met Thr Leu
        435                 440                 445

Ser Gln Glu Gly Ala Gln Asp Ser Phe Pro Leu Gln Gln Lys Ile Leu
    450                 455                 460

Val Cys Ser Leu Met Leu Leu Ile Arg Gln Leu Lys Ile Lys Glu Val
465                 470                 475                 480

Thr Leu Gly Lys Leu Tyr Glu Ala Tyr Ser Lys Val Cys Arg Lys Gln
                485                 490                 495

Gln Val Ala Ala Val Asp Gln Ser Glu Cys Leu Ser Leu Ser Gly Leu
            500                 505                 510

Leu Glu Ala Arg Gly Ile Leu Gly Leu Lys Arg Asn Lys Glu Thr Arg
        515                 520                 525

Leu Thr Lys Val Phe Phe Lys Ile Glu Glu Lys Glu Ile Glu His Ala
    530                 535                 540

Leu Lys Asp Lys Ala Leu Ile Gly Asn Ile Leu Ala Thr Gly Leu Pro
545                 550                 555                 560

(2) INFORMATION FOR SEQ ID NO:3:

(i) SEQUENCE CHARACTERISTICS:
        (A) LENGTH: 1371 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1368

(xi) SEQUENCE DESCRIPTION: SEQ ID NO:3:
```

```
ATG CCA AGC ACC AGG TCT CGG TCT CAA AGC TCC ATT CAG TTT CCC AAG         48
Met Pro Ser Thr Arg Ser Arg Ser Gln Ser Ser Ile Gln Phe Pro Lys
 1               5                  10                  15

AAA AAG ACT TCT CAG ACG CTC GCC AAA GAG GTC TCA CGT GCA AAG AGC         96
Lys Lys Thr Ser Gln Thr Leu Ala Lys Glu Val Ser Arg Ala Lys Ser
             20                  25                  30

AAG TCT GAG ATC TGC TCC TCT GTC TCC CTC CCG CTC TCT CCA CTT CCC        144
Lys Ser Glu Ile Cys Ser Ser Val Ser Leu Pro Leu Ser Pro Leu Pro
         35                  40                  45

AAA GAG CTT CCC CTC AGT CCA CGC AAA CGG CTC GGT GAT GAC AAT CGT        192
Lys Glu Leu Pro Leu Ser Pro Arg Lys Arg Leu Gly Asp Asp Asn Arg
     50                  55                  60

TGC AAC ATT CCT CCG ACA TTA AGC TGC TCC CCA CCC AAG CAG TCT CGC        240
Cys Asn Ile Pro Pro Thr Leu Ser Cys Ser Pro Pro Lys Gln Ser Arg
 65                  70                  75                  80

AAA GAG ACT GGC CAG CCA ACC ACC CCT AAG GGG CGC CGT TTA CTT TTT        288
Lys Glu Thr Gly Gln Pro Thr Thr Pro Lys Gly Arg Arg Leu Leu Phe
                 85                  90                  95

GAT GAG AAC CAG GCT GCA GCA GCG ACA CCA CTA TCC CCC CTC AAG AAG        336
Asp Glu Asn Gln Ala Ala Ala Ala Thr Pro Leu Ser Pro Leu Lys Lys
             100                 105                 110

CTA CAG GAT CCT TAT CTG CTG TCC CCT GTG AGA AAG GGG CAA GAG ACC        384
Leu Gln Asp Pro Tyr Leu Leu Ser Pro Val Arg Lys Gly Gln Glu Thr
         115                 120                 125

CCA CCC AGC TCT CGT AAG CAA AGG AAC AGT GTG GGG GTC CAG CTA TTT        432
Pro Pro Ser Ser Arg Lys Gln Arg Asn Ser Val Gly Val Gln Leu Phe
     130                 135                 140

AAA CAG GAG GGC TCC TGC TAT CAG AAG GCT AAG CAC GCT TTG AAT ACG        480
Lys Gln Glu Gly Ser Cys Tyr Gln Lys Ala Lys His Ala Leu Asn Thr
145                 150                 155                 160

GCT ATA CCA GAG CGC CTG TTG GCT CGT GAG AGT GAG ACT GCA TTT ATC        528
Ala Ile Pro Glu Arg Leu Leu Ala Arg Glu Ser Glu Thr Ala Phe Ile
                 165                 170                 175

AAG ACC TTC CTG ACA AGT CAT GTT TCT GCT GGG AAA GCC GGG AGC CTT        576
Lys Thr Phe Leu Thr Ser His Val Ser Ala Gly Lys Ala Gly Ser Leu
             180                 185                 190

TAC ATA TCT GGT GCT CCT GGA ACT GGC AAA ACT GCG TGC TTG AAT AAG        624
Tyr Ile Ser Gly Ala Pro Gly Thr Gly Lys Thr Ala Cys Leu Asn Lys
         195                 200                 205

CTG CTG CAG GAG ACC AAG GAT GAT CTC AAG CAG TGC AAG ACC GTT TAC        672
Leu Leu Gln Glu Thr Lys Asp Asp Leu Lys Gln Cys Lys Thr Val Tyr
     210                 215                 220

ATC AAC TGC ATG TCA TTG CGC AGC TCC CAG GCA GTG TTT CCG GCT ATA        720
Ile Asn Cys Met Ser Leu Arg Ser Ser Gln Ala Val Phe Pro Ala Ile
225                 230                 235                 240

GCT GAA GAA ATC TCT GGG GGC AAA TCT TCA CTG GCC GCC AAA GAT ATT        768
Ala Glu Glu Ile Ser Gly Gly Lys Ser Ser Leu Ala Ala Lys Asp Ile
                 245                 250                 255

GTA AGG AGT TTG GAG AAG CTG GTG ACT TCA AAG GGT CCA ATC ATC TTG        816
Val Arg Ser Leu Glu Lys Leu Val Thr Ser Lys Gly Pro Ile Ile Leu
             260                 265                 270

CTG GTG TTG GAT GAG ATG GAT CAG CTG GAC AGC AGA GGA CAG GAT GTC        864
Leu Val Leu Asp Glu Met Asp Gln Leu Asp Ser Arg Gly Gln Asp Val
         275                 280                 285

TTG TAC ACC GTG TTT GAG TGG CCT TGG CTT ACA AAT TCT AGG ATG GTT        912
Leu Tyr Thr Val Phe Glu Trp Pro Trp Leu Thr Asn Ser Arg Met Val
     290                 295                 300

TTA ATC GGC ATT GCT AAC GCA TTG GAT TTG ACA GAC CGT ATT TTG CCC        960
Leu Ile Gly Ile Ala Asn Ala Leu Asp Leu Thr Asp Arg Ile Leu Pro
305                 310                 315                 320
```

```
AGG CTA CAA GCT CGA CGT CCG TGC AGA CCA CAG TTG CTC AAC TTT TCT         1008
Arg Leu Gln Ala Arg Arg Pro Cys Arg Pro Gln Leu Leu Asn Phe Ser
            325                 330                 335

CCA TAT ACA AAG GAT CAG ATT GCT ACC ATT CTA CAG GAC AGA CTA AAT         1056
Pro Tyr Thr Lys Asp Gln Ile Ala Thr Ile Leu Gln Asp Arg Leu Asn
            340                 345                 350

ACG GTT TCA GGC GAT CAA GTT CTG GAT AAT GCT GCT ATT CAG TTC TGT         1104
Thr Val Ser Gly Asp Gln Val Leu Asp Asn Ala Ala Ile Gln Phe Cys
            355                 360                 365

GCA AGG AAA ATC TCT GCT GTC TCT GGA GAT GCT CGA AAG GCG CTA GAT         1152
Ala Arg Lys Ile Ser Ala Val Ser Gly Asp Ala Arg Lys Ala Leu Asp
            370                 375                 380

ATC TGC AGG AGA GCT GTT GAA ATT GTC GAA GCG GAT GTC AGG GGC CAG         1200
Ile Cys Arg Arg Ala Val Glu Ile Val Glu Ala Asp Val Arg Gly Gln
385                 390                 395                 400

ACT GTC CTT AAG CCT CTA ACT GAA TGT GCG TCT CCT TGT AAA GAA GTC         1248
Thr Val Leu Lys Pro Leu Thr Glu Cys Ala Ser Pro Cys Lys Glu Val
            405                 410                 415

CCA TTA AAC CCT GTT CCA AAA AAG GTC AGC CTT CCA CAC ATC TCT CGT         1296
Pro Leu Asn Pro Val Pro Lys Lys Val Ser Leu Pro His Ile Ser Arg
            420                 425                 430

GTC CTG TCG GAT GTG TAT GGG GAC AAG ATG GCA AGC CGT GAG GGT TCA         1344
Val Leu Ser Asp Val Tyr Gly Asp Lys Met Ala Ser Arg Glu Gly Ser
            435                 440                 445

AGC GAG AGT TTT CCC TTA CAG CAG AAA                                     1371
Ser Glu Ser Phe Pro Leu Gln Gln
    450                 455

(2) INFORMATION FOR SEQ ID NO:4:

(i) SEQUENCE CHARACTERISTICS:
        (A) LENGTH: 456 amino acids
        (B) TYPE: amino acid
        (D) TOPOLOGY: linear (ii) MOLECULE TYPE: protein (xi) SEQUENCE DESCRIPTION: SEQ ID NO:4:

Met Pro Ser Thr Arg Ser Arg Ser Gln Ser Ser Ile Gln Phe Pro Lys
1               5                   10                  15

Lys Lys Thr Ser Gln Thr Leu Ala Lys Glu Val Ser Arg Ala Lys Ser
            20                  25                  30

Lys Ser Glu Ile Cys Ser Ser Val Ser Leu Pro Leu Ser Pro Leu Pro
        35                  40                  45

Lys Glu Leu Pro Leu Ser Pro Arg Lys Arg Leu Gly Asp Asp Asn Arg
    50                  55                  60

Cys Asn Ile Pro Pro Thr Leu Ser Cys Ser Pro Lys Gln Ser Arg
65                  70                  75                  80

Lys Glu Thr Gly Gln Pro Thr Thr Pro Lys Gly Arg Arg Leu Leu Phe
                85                  90                  95

Asp Glu Asn Gln Ala Ala Ala Thr Pro Leu Ser Pro Leu Lys Lys
            100                 105                 110

Leu Gln Asp Pro Tyr Leu Leu Ser Pro Val Arg Lys Gly Gln Glu Thr
        115                 120                 125

Pro Pro Ser Ser Arg Lys Gln Arg Asn Ser Val Gly Val Gln Leu Phe
    130                 135                 140

Lys Gln Glu Gly Ser Cys Tyr Gln Lys Ala Lys His Ala Leu Asn Thr
145                 150                 155                 160
```

```
Ala Ile Pro Glu Arg Leu Leu Ala Arg Glu Ser Glu Thr Ala Phe Ile
            165                 170                 175

Lys Thr Phe Leu Thr Ser His Val Ser Ala Gly Lys Ala Gly Ser Leu
            180                 185                 190

Tyr Ile Ser Gly Ala Pro Gly Thr Gly Lys Thr Ala Cys Leu Asn Lys
            195                 200                 205

Leu Leu Gln Glu Thr Lys Asp Asp Leu Lys Gln Cys Lys Thr Val Tyr
    210                 215                 220

Ile Asn Cys Met Ser Leu Arg Ser Ser Gln Ala Val Phe Pro Ala Ile
225                 230                 235                 240

Ala Glu Glu Ile Ser Gly Gly Lys Ser Ser Leu Ala Ala Lys Asp Ile
                245                 250                 255

Val Arg Ser Leu Glu Lys Leu Val Thr Ser Lys Gly Pro Ile Ile Leu
            260                 265                 270

Leu Val Leu Asp Glu Met Asp Gln Leu Asp Ser Arg Gly Gln Asp Val
    275                 280                 285

Leu Tyr Thr Val Phe Glu Trp Pro Trp Leu Thr Asn Ser Arg Met Val
    290                 295                 300

Leu Ile Gly Ile Ala Asn Ala Leu Asp Leu Thr Asp Arg Ile Leu Pro
305                 310                 315                 320

Arg Leu Gln Ala Arg Arg Pro Cys Arg Pro Gln Leu Leu Asn Phe Ser
                325                 330                 335

Pro Tyr Thr Lys Asp Gln Ile Ala Thr Ile Leu Gln Asp Arg Leu Asn
                340                 345                 350

Thr Val Ser Gly Asp Gln Val Leu Asp Asn Ala Ala Ile Gln Phe Cys
                355                 360                 365

Ala Arg Lys Ile Ser Ala Val Ser Gly Asp Ala Arg Lys Ala Leu Asp
    370                 375                 380

Ile Cys Arg Arg Ala Val Glu Ile Val Glu Ala Asp Val Arg Gly Gln
385                 390                 395                 400

Thr Val Leu Lys Pro Leu Thr Glu Cys Ala Ser Pro Cys Lys Glu Val
                405                 410                 415

Pro Leu Asn Pro Val Pro Lys Lys Val Ser Leu Pro His Ile Ser Arg
                420                 425                 430

Val Leu Ser Asp Val Tyr Gly Asp Lys Met Ala Ser Arg Glu Gly Ser
    435                 440                 445

Ser Glu Ser Phe Pro Leu Gln Gln
    450                 455

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:5:

CCTCTCAGCC CCAGGAAACG                                           20

(2) INFORMATION FOR SEQ ID NO:6:

(i) SEQUENCE CHARACTERISTICS:
        (A) LENGTH: 24 amino acids
        (B) TYPE: amino acid
        (C) STRANDEDNESS: single
        (D) TOPOLOGY: linear
```

```
            -continued (ii) MOLECULE TYPE: peptide (xi) SEQUENCE DESCRIPTION: SEQ ID NO:6:

Gly Gly Ile Gly Cys Cys Cys Cys Gly Gly Ile Ala Cys Cys Gly
    1               5                   10                  15

Gly Ile Ala Ala Ala Ala Cys Cys
                20

(2) INFORMATION FOR SEQ ID NO:7:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Ala Thr Cys Gly Thr Gly Cys Thr Cys Gly Ala Cys Gly Ala Gly Ala
    1               5                   10                  15

Thr Gly Gly (2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Ala Gly Ala Ala Ala Ile Cys Gly Gly Thr Cys Ile Gly Thr Cys Ala
    1               5                   10                  15

Thr Gly Thr Cys
                20
```